(12) United States Patent
Switzer et al.

(10) Patent No.: US 12,690,757 B2
(45) Date of Patent: Jul. 28, 2026

(54) METHOD AND APPARATUS FOR INSTRUMENT PROPULSION

(71) Applicant: Endogene Limited, Brighton (AU)

(72) Inventors: Anthony Switzer, Glenbrook (AU); Mikhail Soutorine, Melbourne (AU)

(73) Assignee: ENDOGENE LIMITED, Brighton (AU)

( * ) Notice: Subject to any disclaimer, the term of this patent is extended or adjusted under 35 U.S.C. 154(b) by 602 days.

(21) Appl. No.: 18/343,567

(22) Filed: Jun. 28, 2023

(65) Prior Publication Data

US 2024/0000297 A1     Jan. 4, 2024

Related U.S. Application Data

(63) Continuation of application No. 16/607,640, filed as application No. PCT/AU2018/050380 on Apr. 26, 2018, now abandoned.

(30) Foreign Application Priority Data

| Apr. 27, 2017 | (AU) | ................................. | 2017901531 |
| Feb. 16, 2018 | (AU) | ................................. | 2018900500 |

(51) Int. Cl.
*A61B 1/00* (2006.01)
*A61B 1/018* (2006.01)
(Continued)

(52) U.S. Cl.
CPC .......... *A61B 1/018* (2013.01); *A61B 1/00133* (2013.01); *A61B 1/00137* (2013.01);
(Continued)

(58) Field of Classification Search
CPC ............ A61B 1/00154; A61B 1/00156; A61B 1/0016
See application file for complete search history.

(56) References Cited

U.S. PATENT DOCUMENTS

| 3,485,237 A | 12/1969 | Bedford |
| 4,176,662 A | 12/1979 | Frazer |
| | (Continued) | |

FOREIGN PATENT DOCUMENTS

| CN | 1688240 A | 10/2005 |
| CN | 101112300 A | 1/2008 |
| | (Continued) | |

OTHER PUBLICATIONS

International Search Report for corresponding International application No. PCT/AU2018/050380 mailed Jul. 2, 2018.

(Continued)

*Primary Examiner* — Colin T. Sakamoto
(74) *Attorney, Agent, or Firm* — Crowell & Moring LLP

(57) ABSTRACT

Embodiments generally relate to propulsion tube units and propulsion devices for progressing instruments along passages, and associated methods of use. For example, the instruments may include, tools, sensors, probes and/or monitoring equipment for medical use (such as endoscopy) or industrial use (such as mining).

In some embodiments, the propulsion device may comprise an elongate tube defining a channel configured to accommodate a liquid and a pressure actuator in communication with the channel. The pressure actuator may be configured to selectively adjust a pressure of the liquid in the channel to alternatingly: reduce the pressure to induce cavitation and form gas bubbles in the liquid; and increase the pressure to collapse some or all of the gas bubbles back into the liquid, thereby accelerating at least part of the liquid towards the first end of the tube and transferring momentum to the tube to progress the tube along the passage.

20 Claims, 12 Drawing Sheets

(51) Int. Cl.

| | | |
|---|---|---|
| *A61B 1/12* | (2006.01) | |
| *A61L 29/14* | (2006.01) | |
| *F04B 43/09* | (2006.01) | |

(52) U.S. Cl.

CPC ...... *A61B 1/00147* (2013.01); *A61B 1/00154* (2013.01); *A61B 1/00156* (2013.01); *A61B 1/12* (2013.01); *A61L 29/146* (2013.01); *F04B 43/09* (2013.01); *A61B 2560/04* (2013.01); *A61B 2562/0204* (2013.01); *A61L 2420/08* (2013.01)

(56) References Cited

U.S. PATENT DOCUMENTS

| | | | |
|---|---|---|---|
| 4,207,872 | A | 6/1980 | Meiri et al. |
| 5,480,398 | A | 1/1996 | Eggers |
| 2002/0058951 | A1 | 5/2002 | Fielder |
| 2002/0111535 | A1 | 8/2002 | Kim et al. |
| 2007/0100412 | A1 | 5/2007 | Dwyer et al. |
| 2007/0179432 | A1 | 8/2007 | Bar Or et al. |
| 2008/0097292 | A1 | 4/2008 | Cabiri et al. |
| 2010/0256448 | A1 | 10/2010 | Smith et al. |
| 2013/0172679 | A1 | 7/2013 | Ashida |
| 2014/0378947 | A1* | 12/2014 | Soyama ................ A61B 1/126 604/257 |
| 2015/0013304 | A1* | 1/2015 | Wang ..................... B82B 1/006 60/770 |
| 2015/0119639 | A1 | 4/2015 | Ebata |

| | | | |
|---|---|---|---|
| 2015/0202423 | A1 | 7/2015 | Adenusi |
| 2015/0359416 | A1 | 12/2015 | Simchony et al. |
| 2016/0015247 | A1 | 1/2016 | Irion et al. |
| 2016/0380523 | A1 | 12/2016 | Hunter et al. |

FOREIGN PATENT DOCUMENTS

| | | | | |
|---|---|---|---|---|
| CN | 102149312 | A | 8/2011 | |
| CN | 103517665 | A | 1/2014 | |
| CN | 104105512 | A | 10/2014 | |
| CN | 104434005 | A | 3/2015 | |
| CN | 106132271 | A | 11/2016 | |
| DE | 40 14 998 | A1 | 11/1991 | |
| JP | S63 142189 | A | 6/1988 | |
| JP | 2002-125925 | A | 5/2002 | |
| JP | 2005-176941 | A1 | 7/2005 | |
| JP | 2005-535403 | A | 11/2005 | |
| JP | 2015-123355 | A | 7/2015 | |
| JP | 2016-509592 | A | 3/2016 | |
| JP | S 6173632 | B2 | 8/2017 | |
| JP | S 6230211 | B2 | 11/2017 | |
| WO | WO 2003/053225 | A1 | 7/2003 | |
| WO | WO 2004/047903 | A2 | 6/2004 | |
| WO | WO-2009135251 | A1 * | 11/2009 | ........ A61M 25/0032 |

OTHER PUBLICATIONS

Written Opinion of the International Searching Authority for corresponding International application No. PCT/AU2018/050380 mailed Jul. 2, 2018.

* cited by examiner

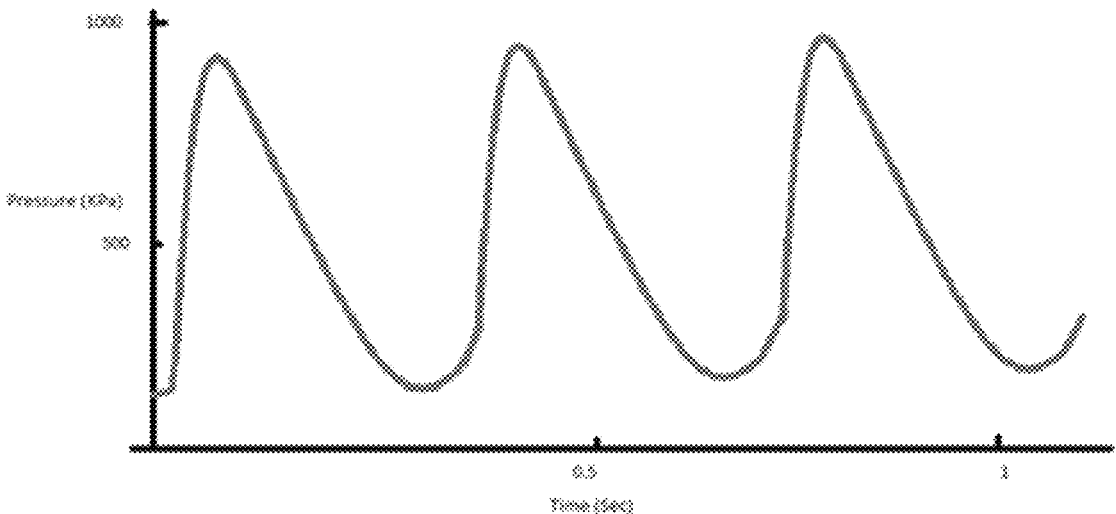
Fig.12
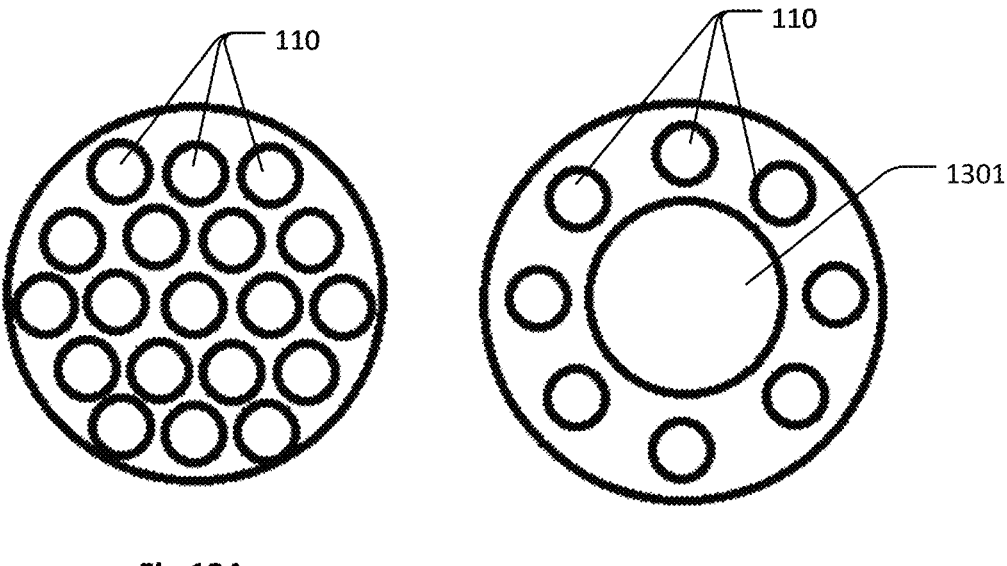
Fig.13A                              Fig.13B

METHOD AND APPARATUS FOR INSTRUMENT PROPULSION

CROSS-REFERENCE TO RELATED APPLICATIONS

This application is a continuation of U.S. application Ser. No. 16/607,640, filed Aug. 24, 2020, which is the U.S. national stage application of International Application No. PCT/AU2018/050380, filed Apr. 26, 2018, which claims priority to Australian Patent Application No. 2018900500, filed on Feb. 16, 2018, and which claims priority to Australian Patent Application No. 2017901531, filed Apr. 27 2017, all of which are hereby incorporated by reference in their entirety.

TECHNICAL FIELD

Embodiments generally relate to propulsion tube units and propulsion devices for progressing instruments along passages, and associated methods of use. For example, the instruments may include, tools, sensors, probes and/or monitoring equipment for medical use (such as endoscopy) or industrial use (such as mining). The described embodiments may also be suitable for applications in other fields to progress an instrument along a passage.

BACKGROUND

There are a number of existing methods and apparatus for progressing instruments along passages including applications in mining and in medicine, such as endoscopy. There are a number of difficulties with progressing conventional endoscopic equipment along a tract or lumen in a patient, and these difficulties may carry associated risks of causing damage to the patient.

It is desired to address or ameliorate one or more shortcomings or disadvantages associated with existing propulsion devices for progressing instruments along passages, or to at least provide a useful alternative.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

Some embodiments relate to a propulsion device for progressing an instrument along a passage, the propulsion device comprising:

an elongate tube comprising a first end and a second end opposite the first end, the tube defining a channel configured to accommodate a liquid, a first end of the channel being closed at or near the first end of the tube and a second end of the channel being defined by the second end of the tube; and a pressure actuator in communication with the second end of the channel and configured to selectively adjust a pressure of the liquid in the channel to alternatingly:

reduce the pressure to induce cavitation and form gas bubbles in the liquid; and increase the pressure to collapse some or all of the gas bubbles back into the liquid, thereby accelerating at least part of the liquid towards the first end of the tube and transferring momentum to the tube to progress the tube along the passage.

Some embodiments relate to a propulsion tube unit comprising:

an elongate tube comprising a first end and a second end opposite the first end, the tube defining a channel configured to accommodate a liquid, a first end of the channel being closed at or near the first end of the tube and a second end of the channel being defined by the second end of the tube; and a piston assembly connected to the second end of the tube, the piston assembly comprising:

a body defining a bore in fluid communication with the channel of the tube; and a movable piston disposed within the bore and configured to seal against an internal surface of the bore, wherein the piston assembly and the tube cooperate to define a sealed vessel containing a selected mass of liquid and a selected mass of gas.

The piston assembly may be configured for cooperation with an actuator to effect movement of the piston to selectively adjust a pressure of the liquid in the channel to alternatingly: reduce the pressure to induce cavitation and form gas bubbles in the liquid; and increase the pressure to collapse some or all of the gas bubbles back into the liquid, thereby accelerating at least part of the liquid towards the first end of the tube and transferring momentum to the tube to progress the tube along the passage.

In some embodiments, the propulsion device or propulsion tube unit may comprise one or more mechanisms configured to promote cavitation in one or more regions of the channel when the pressure is reduced, wherein the one or more regions extend along at least part of a length of the channel. The one or more mechanisms may be configured to promote cavitation in a plurality of regions spaced along at least part of the length of the channel. The one or more mechanisms may comprise a surface variation on an internal surface of the channel.

The surface variation may comprises a coating. The coating may comprise a hydrophobic material. The coating may comprise a catalytic material. The coating may comprise one or more coatings selected from: octadecyltrichlorosilane, silane compounds, Parylene C, flouropolymers, PTFE (Teflon™), manganese oxide polystyrene (MnO2/PS), nano-composite zinc oxide polystyrene (ZnO/PS), nano-composite precipitated calcium carbonate, fluorinated acrylate oligomers, urethane, acrylic, polyvinylpyrrolidone (PVP), polyethylene oxide, combinations of hydroxyethyl-methacrylate, and acrylamides, or other hydrophobic compounds.

The surface variation may comprise a topographical variation. The topographical variation may have a surface roughness in the range of about 0.1 $\mu$m to 500 $\mu$m, about 0.5 $\mu$m to 100 $\mu$m, or about 1 $\mu$m to 10 $\mu$m, for example.

The topographical variation may comprises a scratched or pitted surface. The topographical variation may define a plurality of V-shaped channels. A characteristic angle of the V-shaped channels may be in the range of about 10° to 90°, about 30° to 60°, or about 40° to for example. An average width of the V-shaped channels may be in the range of about 1 $\mu$m to 10 $\mu$m, or about 2 $\mu$m to 4 $\mu$m, for example.

The topographical variation may define a plurality of conical pits. A characteristic angle of the conical pits may be in the range of about 10° to 90°, about 30° to 60°, or about 40° to 50°, for example. An average width of the conical pits may be in the range of about 1 µm to 10 µm, or about 2 µm to 4 µm, for example.

The topographical variation may define a plurality of protrusions. An average height of the protrusions may be in the range of about 0.1 µm to 1 mm, about 1 µm to 500 µm, or about 10 µm to 100 µm, for example. An average width of the protrusions may be in the range of about to 500 µm, about 0.5 µm to 100 µm, or about 1 µm to 10 µm, for example. An average distance between adjacent protrusions may be in the range of about 0.1 µm to 500 µm, about to 100 µm, or about 1 µm to 10 µm, for example.

In some embodiments, the protrusions may comprise nanowires or hollow nanotubes which may be formed of materials such as carbon or silicon, for example.

For nanowire, the width of the protrusions may be in the range of about 10 nm to 500 nm, about 20 nm to 300 nm, or about 100 nm to 200 nm; the length or height of the protrusions 835 may be in the range of about 0.1 µm to 100 µm, about 1 µm to 50 µm, or about 10 µm to 20 µm; and the average spacing between protrusions may be in the range of about 10 nm to 10 µm, about 10 nm to 100 nm, or about 100 nm to 1 µm, for example.

For nanotubes, the width of the protrusions may be in the range of about 10 nm to 100 nm, about 10 nm to 50 nm, or about 20 nm to 40 nm; the length or height of the protrusions may be in the range of about 1 µm to 50 µm, about 5 µm to 30 µm, or about 10 µm to 20 µm; the pore size (or internal diameter) of the protrusions may be in the range of about 1 µm to 40 µm, about 5 µm to 30 µm, or about 10 µm to 20 µm; and the average spacing between protrusions may be in the range of about 10 nm to 10 µm, about 10 nm to 100 nm, or about 100 nm to 1 µm, for example.

The topographical variation may define a porous surface. The porous surface may comprise a foam, sintered material or other porous material, for example. An average pore size of the porous surface may be in the range of about 10 nm to 200 µm, about 20 nm to 250 nm, about to 150 nm, about 10 µm to about 200 µm, or about 50 µm to about 100 µm, for example. The porous surface may comprise a layer of porous material. The thickness of the porous layer may be in the range of about 10 µm to 1 mm, or about 50 µm to 100 µm, for example.

The one or more mechanisms may comprise a variation in a thermal conductivity of a wall of the tube along the length of the channel. The thermal conductivity of the wall may vary along the length of the channel over a range of about 0.25 Wm$^{-1}$K$^{-1}$ to 240 Wm$^{-1}$K$^{-1}$.

The one or more mechanisms may comprise one or more acoustic transducers. The one or more of the acoustic transducers may be disposed within a wall of the tube. The one or more of the acoustic transducers may be disposed outside of a wall of the tube. An operating frequency of the acoustic transducers may be in the range of about 1 kHz to 100 kHz. A power associated with insonation energy directed to a lumen of the channel by the acoustic transducers may be in the range of about 10 mW to 100 mW.

In some embodiments, the propulsion device may be configured for progressing a medical instrument along a lumen within a patient.

In some embodiments, the channel may be a continuous enclosed channel extending from the first end of the tube to the second end of the tube. The tube may be reinforced against expansion or contraction due to internal pressure changes. The tube may be formed of a material suitable for sterilisation.

In some embodiments, the propulsion device may comprise a plurality of tubes according to any one of the described embodiments extending side by side.

In some embodiments, the pressure actuator may comprise a flexible membrane defining a sealed chamber and a driving mechanism configured to deform the flexible membrane to selectively adjust the pressure of the liquid in the channel.

In some embodiments, the pressure actuator may comprise a piston assembly including a moveable piston disposed within a bore of the piston assembly; and a driving mechanism configured to drive the piston of the piston assembly to selectively adjust the pressure of the liquid in the channel. The piston assembly may be connected to the tube to form a sealed tube unit containing the liquid, and the piston assembly may be removably coupleable to the driving mechanism.

Some embodiments relate to a propulsion tube unit comprising one or more of the tubes according to any one of the described embodiments; and a piston assembly connected to the second end of the tube, the piston assembly comprising:
a body defining a bore in fluid communication with the channel of each of the one or more tubes; and
a movable piston disposed within the bore and configured to seal against an internal surface of the bore.

Some embodiments relate to a propulsion tube unit comprising: one of the tubes according to any one of the described embodiments; and a movable piston disposed within the channel at or near the second end of the tube and configured to seal against an internal surface of the channel.

In some embodiments, the piston assembly and the one or more tubes may cooperate to define a sealed vessel containing a selected mass of liquid and a selected mass of gas. The selected masses of liquid and gas may be chosen for a particular length and diameter of the tube. The liquid and gas may be held at a predetermined pressure not significantly higher than a typical channel pressure during operation.

Some embodiments relate to a drive console comprising:
a housing defining a socket configured to receive and engage a propulsion tube unit according to any one of the described embodiments;
an actuator configured to engage the piston; and
a controller configured to operate the actuator to move the piston to selectively adjust a pressure within the channel of the tube.

Some embodiments relate to a method of progressing an instrument along a passage, the method comprising selectively adjusting a pressure of a liquid within a tube connected to the instrument to successively induce cavitation of gas bubbles in the liquid and subsequently collapse the gas bubbles back into the liquid to accelerate the liquid within the tube, transfer momentum from the liquid to the tube, and progress the tube along the passageway.

BRIEF DESCRIPTION OF DRAWINGS

Exemplary embodiments will now be described in detail with respect to the drawings, in which:

FIG. 12 shows an exemplary pressure cycle illustrating the pressure applied to the liquid in the tube, according to some embodiments;

FIGS. 13A and 13B show cross-sections of two devices with a plurality of tubes illustrating different arrangements of the tubes, according to some embodiments;

DESCRIPTION OF EMBODIMENTS

Embodiments generally relate to propulsion devices for progressing instruments along passages, and associated methods of use. For example, the instruments may include, tools, sensors, probes and/or monitoring equipment for medical use (such as endoscopy) or industrial use (such as mining). The described embodiments may also be suitable for applications in other fields to progress an instrument along a passage.

Figure 1:
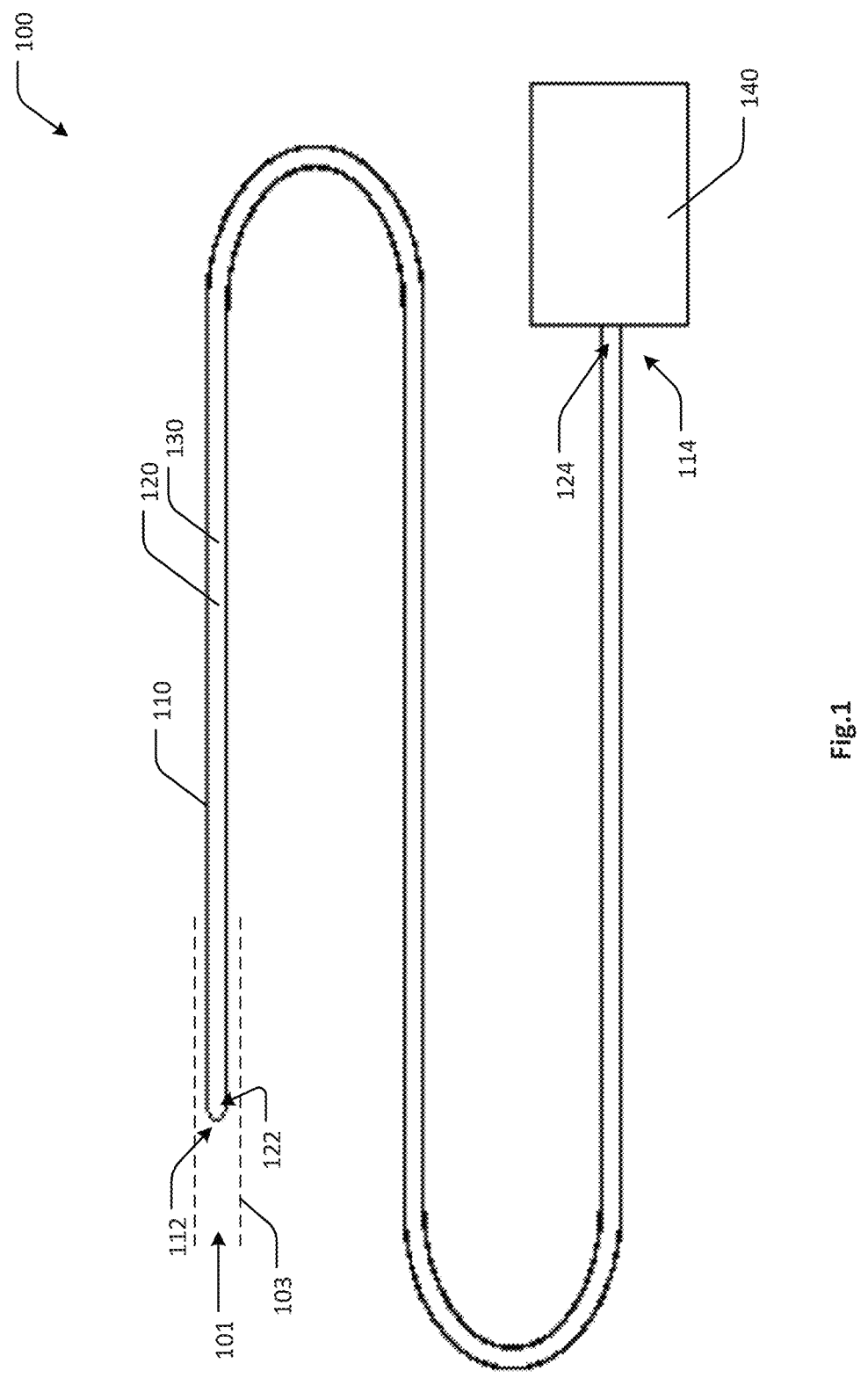
FIG. 1 is a schematic diagram of a propulsion device according to some embodiments.

Referring to FIG. 1, a propulsion device 100 is shown according to some embodiments. The propulsion device 100 comprises an elongate tube 110 defining a lumen or channel 120 configured to accommodate a liquid 130, and a pressure actuator 140 configured to selectively adjust a pressure of the liquid 130 in the channel 120, such as by varying the pressure, optionally varying the pressure continuously.

A first or distal end 122 of the channel 120 is closed at or near a first or distal end 112 of the tube 110. The distal end 112 of the tube 110 is shown disposed in a channel or lumen 101 of a passage 103 in FIG. 1.

In some embodiments, the tube 110 may be configured to be inserted into and through a biological tract, such as a lumen 101 of a passage 103 of a patient. Examples of such biological tracts include the oesophagus, stomach, bowel, colon, small intestine, large intestine, duodenum, or any one or more passages of the gastro-intestinal system. In some embodiments, the tube 110 may be configured for insertion into and through another passage 103 in a patient, such as blood vessels, veins or arteries, for example. In some embodiments, the tube 110 may be configured for human medical applications or veterinary applications. In some embodiments, the tube 110 may be configured for industrial applications, such as for use in plumbing pipes, wall cavities, cable tracks, machinery, mining or wellbores, for example.

Figure 16:
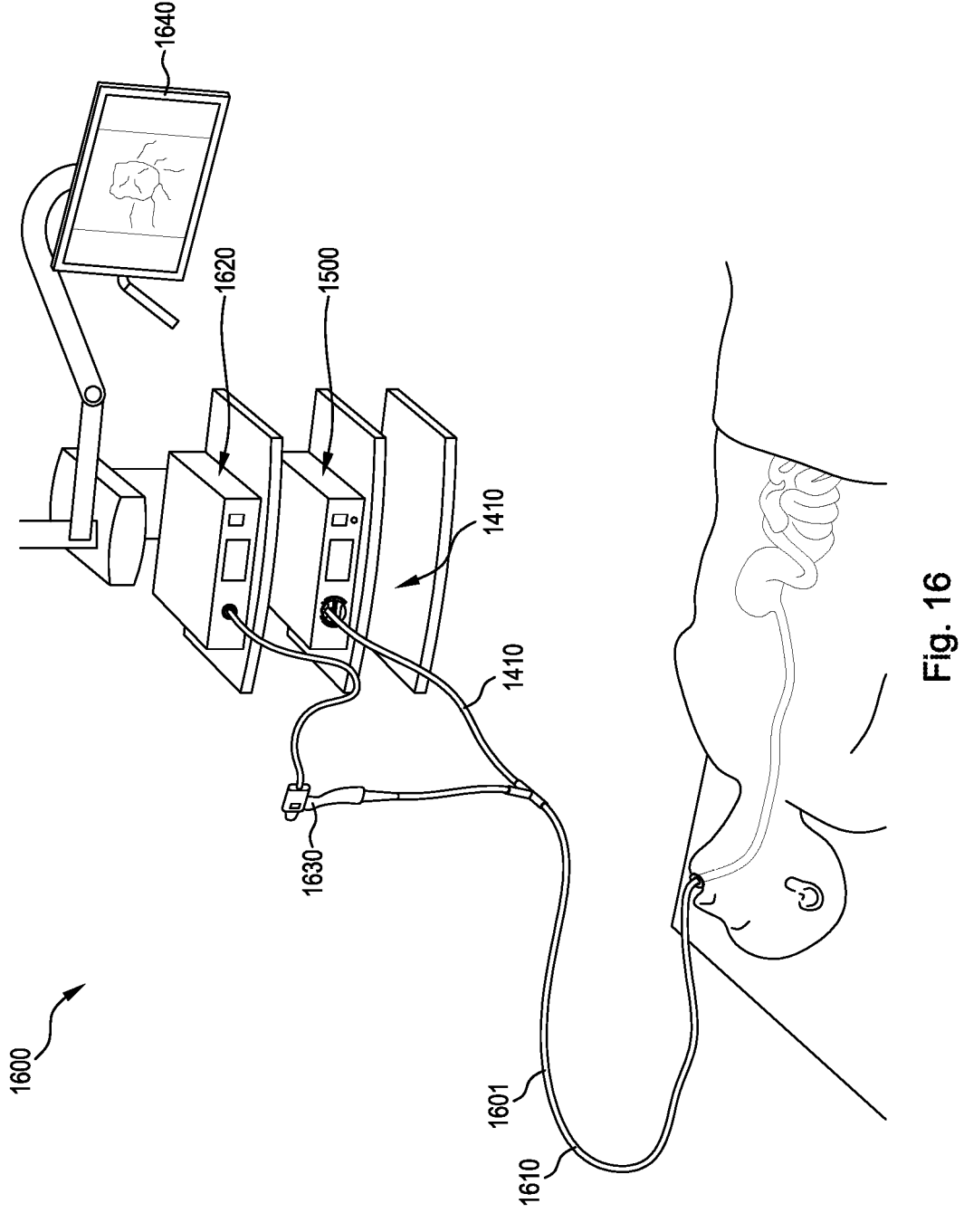
FIG. 16 shows an endoscopic system including the propulsion device of FIG. 14, according to some embodiments.

In some embodiments, the tube 110 may be configured to be accommodated within an insertion tube of an endoscope, and the insertion tube configured to be inserted into a passage 103, such as a passage in a patient. An example of such an arrangement is illustrated in FIG. 16. The tube 110 of the propulsion device 100 may be accommodated within a propulsion tube channel (not shown) within the insertion tube. In some embodiments, the propulsion tube channel may be concentric or coaxial with the outer diameter of the insertion tube, and may extend along a central longitudinal axis of the insertion tube. In some embodiments, the propulsion tube channel may be radially offset from the central axis of the insertion tube.

The pressure actuator 140 is in communication with a second or proximal end 124 of the channel 120 at or near a second or proximal end 114 of the tube 110 opposite the distal end 112. The channel 120 may comprise a continuous enclosed channel extending from the first end 112 of the tube 110 to the second end 114 of the tube 110.

The pressure actuator 140 may comprise any suitable device configured to selectively adjust a pressure of the liquid 130 in the channel 120, such as a reciprocating piston, for example. In some embodiments, the pressure actuator 140 may comprise a piston driven by a motor, such as a linear motor, controlled by a controller (not shown).

The pressure actuator 140 may be configured to gradually reduce the pressure within the channel 120 to induce cavitation and form gas bubbles in the liquid 130, and then to suddenly increase the pressure to compress and collapse the gas bubbles back into the liquid 130, thereby accelerating at least part of the liquid 130 towards the first end 112 of the tube 110, such that momentum is transferred from the liquid to the tube 110 to progress the tube 110 along a passage.

In some embodiments, when the channel 120 is at an initial or base pressure, there may be volumes of gas and liquid 130 within the channel 120, and the pressure actuator 140 may be controlled to increase the pressure to compress and dissolve part or all of the gas into the liquid 130. In some embodiments, the channel 120 may be entirely filled with the liquid 130, and the pressure actuator 140 may reduce the pressure to induce cavitation of gas out of the liquid 130. In various embodiments, the base pressure may be set: at or near atmospheric pressure; significantly higher than atmospheric pressure; or significantly lower than atmospheric pressure.

The pressure actuator 140 may be configured to adjust the pressure in a repeating cycle to induce cavitation of gas bubbles out of the liquid 130 and subsequently compress part or all of the gas back into the liquid 130. In various applications, the difference between the maximum pressure in the channel 120 and the minimum pressure in the channel 120 may be in the range of about 10 kPa to 100 MPa, about 10 kPa to 100 kPa, about 100 kPa to 1 MPa, about 1 MPa to about 10 MPa, or about 10 MPa to about 100 MPa, for example. In some embodiments, the maximum pressure may be above, below or close to atmospheric pressure. In some embodiments, the minimum pressure may be above, below or close to atmospheric pressure but having a non-zero difference from the maximum pressure.

For example, for gastro-intestinal applications, the channel pressure may vary from 100 kPa below atmospheric pressure to 1000 kPa above atmospheric pressure; for cardiovascular applications, the channel pressure may vary from 20 kPa below atmospheric pressure to 300 kPa above atmospheric pressure; for industrial applications, the channel pressure may vary from 1000 kPa below atmospheric pressure to 10000 kPa above atmospheric pressure.

The liquid 130 in the channel 120 may comprise any one or more of: a pure liquid, a solution, a gas/liquid solution (i.e., a gas dissolved in liquid), a mixture of gas and liquid, a mixture of liquid and solid particles, such as a suspension, and a mixture of two or more miscible or immiscible liquids, for example. In some embodiments, the volumetric ratio of gas to liquid at atmospheric pressure may be in the range of about 0.1% to 10%, about 0.5% to 5%, or about 1% to 2%, for example.

The liquid 130 may comprise any suitable liquids, gases, solid particles or solutions, such as: water, ethanol, carbon dioxide, nitrogen, air, nitric oxide, argon, salts, sodium chloride, potassium formate, acids, acetic acid, or lithium metatungstate, for example.

Different liquids may be suitable for different applications. For example, in medical applications, preferred liquids may be biocompatible, non-toxic (or have very low toxicity), non-pyrogenic, non-inflammatory, not highly osmotic, relatively inert, and be suitable for operation at relatively low pressures and at temperatures similar to the typical temperature of a patient. For example, water, ethanol, carbon dioxide, nitrogen, air, nitric oxide, argon.

In industrial applications where biocompatibility is not required, liquids with higher densities may be preferred, such as aqueous solutions of inert inorganic compounds, for example. One suitable high density liquid may be an aqueous solution of lithium metatungstate which has high density, low viscosity, and good thermal stability.

In various embodiments, the tube 110 may be formed of different materials depending on their suitability for a given application. For example, for medical applications, the tube 110 may be formed of a non-toxic material which is sufficiently flexible to bend around corners or turns in a passage within the body of a patient.

Some examples of materials which may be used to form the tube 110 in different applications include: polymers, plastics, polyethylene, high density polyethylene, polytetrafluoroethylene, vinyl, nylon, rubber, elastomers, resins or composite materials comprising textiles impregnated with polymers, elastomers or resins. Polymers containing voids (foams) in the internal structure may also be used to increase flexibility such as extruded polytetrafluoroethylene (ePTFE). Composite layering of these materials may also be used to increase strength maintain flexibility and resist internal pressure or kinking.

A wall 118 of the tube 110 should have a strength and thickness sufficient to withstand the expected range of pressure differentials for a given application. In some embodiments, the tube 110 or tube wall 118 may be reinforced to mitigate against expansion and/or contraction of the tube due to pressure changes. Any suitable reinforcing material may be used, such as high strength fibres or ultra-high molecular weight polyethylene, for example.

Referring to FIGS. 2A to 2F, a segment of the tube 110 of the propulsion device 100 is shown according to some embodiments, illustrating the cavitation process in a series of diagrams.

Figures 2A, 2B, 2C, 2D, 2E, 2F:
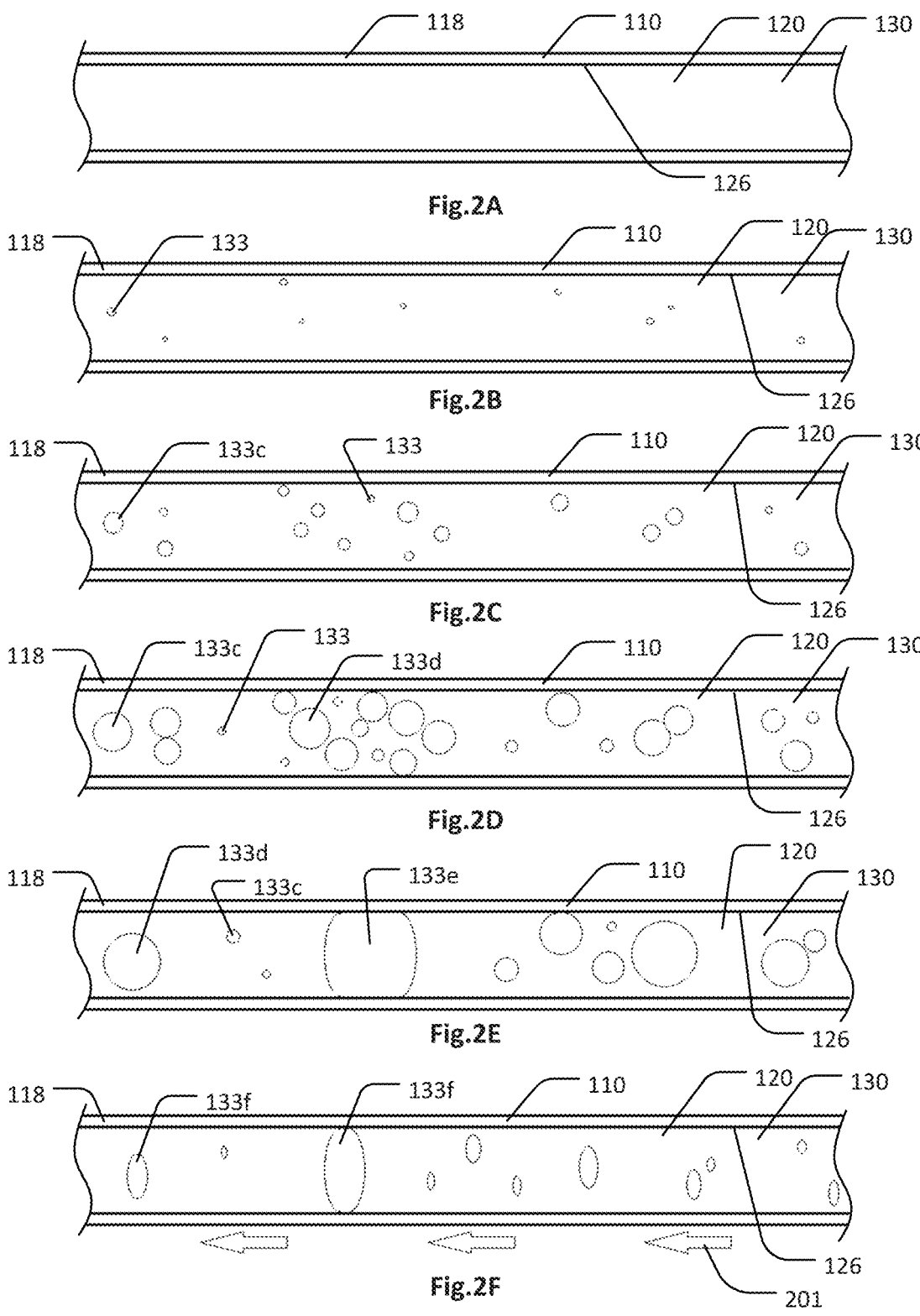
FIGS. 2A to 2F are a series of longitudinal sections of a portion of tube of a propulsion device showing a cycle of nucleation and cavitation of gas bubbles within a liquid contained within the tube, and subsequent collapse of the gas bubbles back into the liquid, according to some embodiments.

Referring to FIG. 2A, at an initial or base pressure, the channel 120 may be substantially or entirely filled with the liquid 130 with little or no gas within the channel 120. (Although, in some embodiments, there may be a significant volume of gas present in the channel at the base pressure).

When the pressure in the channel 120 is gradually reduced by the pressure actuator 140, gas bubbles 133 may begin to form in the liquid 130 within the channel 120, as shown in FIG. 2B. The gas bubbles 133 may comprise gas that was previously dissolved in the liquid 130 and/or vapour (i.e., a gas phase of the liquid 130). The bubbles 133 may form through homogeneous nucleation or through heterogeneous nucleation in the liquid 130 on nucleation sites, such as particles suspended in the liquid 130 and/or at nucleation sites on an inner surface 126 of the tube 110.

As the pressure is reduced further, the bubbles 133 may grow in volume to form larger bubbles 133*c*, as shown in FIG. 2C, and new bubbles 133 may continue to be formed through nucleation. Some of the bubbles 133, 133*c* may coalesce to form even larger bubbles 133*d*, as shown in FIG. 2D.

Under certain conditions, the bubbles 133 may coalesce to form a large bubble 133*e* which spans a lumen of the channel 120, as shown in FIG. 2E. That is, the spanning bubble 133*e* may take up the entire lumen of the channel 120 in a region of the channel 120 such that different portions of the liquid 130 are separated on either side of the bubble 133*e*. It may be desirable to encourage or promote the formation of such spanning bubbles 133*e* in the channel 120, as this may enhance or increase the propulsive effect by increasing the acceleration of the liquid 130 during the sudden increase of pressure, and thus increasing the kinetic energy imparted to the liquid 130 and the momentum transferred to the tube 110.

When the pressure is increased (i.e., during compression) the liquid 130 is accelerated in a distal direction (i.e., towards the first or distal end 122 of the channel 120), as indicated by arrows 201 in FIG. 2F. Due to the relatively high compressibility of the gas bubbles 133, which is orders of magnitude higher than the relatively low compressibility of the liquid 130, the liquid 130 is allowed to accelerate quickly and compress the bubbles 133, as shown in FIG. 2F.

When the bubbles 133 are compressed, they experience a sudden increase in pressure and density, and collapse (i.e., dissolve and/or condense) back into the liquid 130, as shown in FIG. 2A. The rate of dissolution/collapse of the bubbles 133 into the liquid 130 may be increased by increasing the total surface area of the gas-liquid interfaces. Therefore, it may be desirable to encourage or promote the formation of many bubbles 133, and preferably many spanning bubbles 133*e*.

There are a number of ways in which the likelihood of the formation of spanning bubbles 133e may be increased, several of which are discussed below. For example, in some embodiments, one or more additives may be included in the liquid 130 to enhance bubble coalescence. In some embodiments, the internal diameter of the channel 120 may be selected to be relatively small so that only relatively small bubble volumes are required to span the lumen. However, the internal diameter of the lumen should still be large enough to allow the liquid 130 to flow along the channel 120 when the pressure is suddenly increased (i.e., not be too limited by capillary resistance). In some embodiments, the propulsion device 100 may comprise a plurality of tubes 110 extending side by side with each other, and each defining a channel 120. This may allow the internal diameter of each channel 120 to be relatively small while maintaining a relatively high total mass of liquid 130 within the tubes 110.

In some embodiments, cavitation, bubble nucleation and/or bubble coalescence may be enhanced, encouraged or promoted in certain regions of the channel 120.

In some embodiments, the propulsion device 100 may comprise one or more mechanisms configured to promote cavitation, bubble nucleation and/or bubble coalescence in one or more regions of the channel when the pressure is reduced. The one or more regions may extend along at least part of a length of the channel 120. For example, the one or more mechanisms may be configured to promote cavitation, bubble nucleation and/or bubble coalescence in a plurality of regions spaced along the length of the channel 120.

In some embodiments, each region where cavitation is promoted may extend along part of the channel length by a distance of between about 10% and 400% of an internal diameter of the channel 120, optionally about 30% and 300%, optionally about 50% and 200%. In some embodiments, a distance between adjacent regions where cavitation is promoted may be greater than the internal diameter of the channel 120 by a factor of about 2 to 50, about 5 to 30, or about 10 to 20, for example.

Referring to FIGS. 3A to 3G, a segment of the tube 110 of the propulsion device 100 is shown according to some embodiments, illustrating the cavitation process in a series of diagrams. The cavitation process is similar to that described in relation to FIGS. 2A to 2F; however, the tube 110 shown in FIGS. 3A to 3G also includes one or more mechanisms 330 configured to promote cavitation, bubble nucleation and/or bubble coalescence in one or more regions of the channel 120 when the pressure is reduced.

Figures 3A, 3B, 3C, 3D, 3E, 3F, 3G:
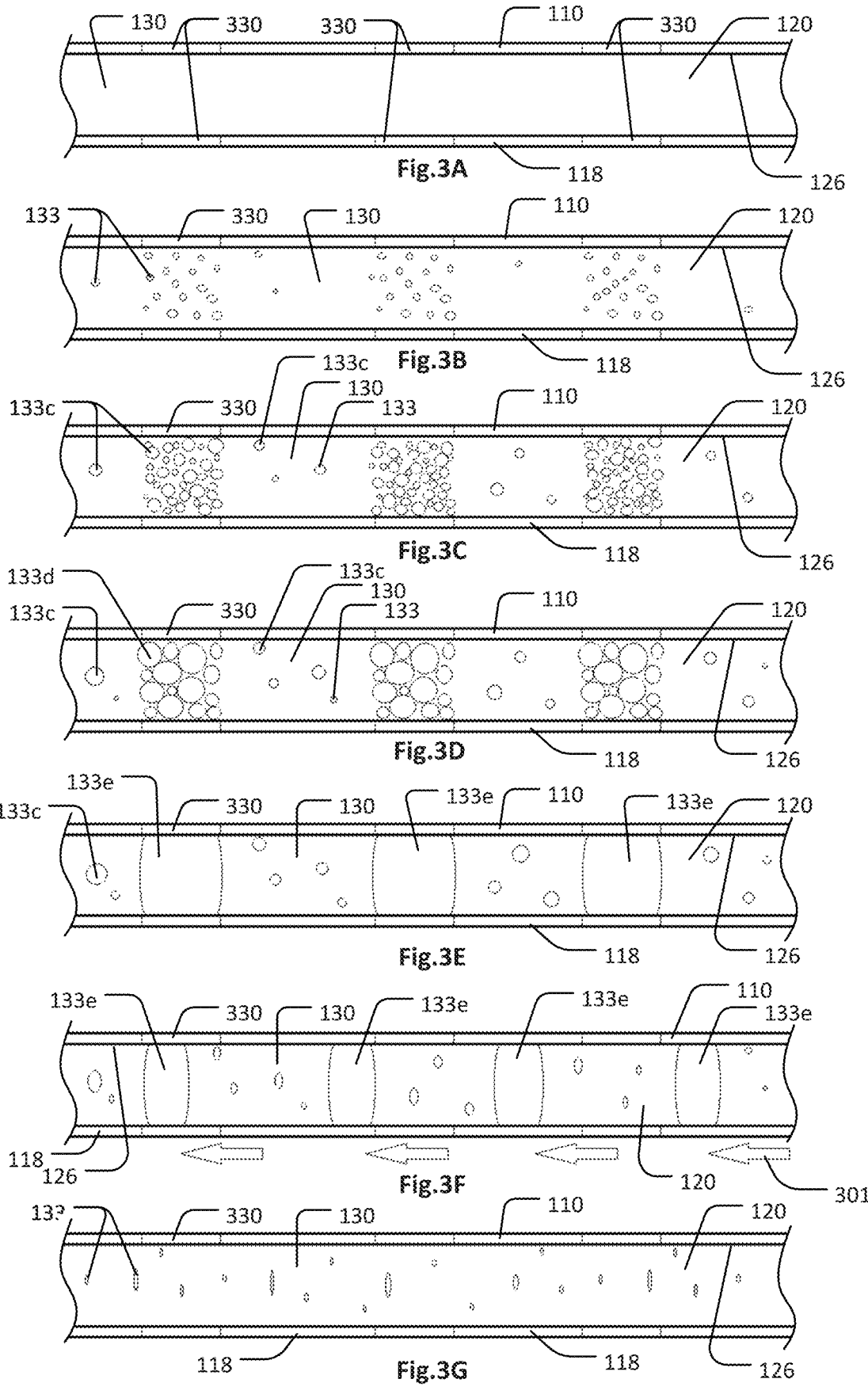
FIGS. 3A to 3G are a series of longitudinal sections of a portion of tube of a propulsion device showing a cycle of nucleation and cavitation of gas bubbles within a liquid contained within the tube, and subsequent collapse of the gas bubbles back into the liquid, according to some embodiments.

Referring to FIG. 3A, at the base pressure, the channel 120 may be substantially or entirely filled with the liquid 130, with little or no gas within the channel 120.

When the pressure in the channel 120 is gradually reduced by the pressure actuator 140, gas bubbles 133 may begin to form in the liquid 130 within the channel 120, as shown in FIG. 3B. Some bubbles 133 may form randomly throughout the liquid 130; however, the likelihood of bubbles 133 forming will be higher in the regions of the cavitation-promoting mechanisms 330.

As the pressure is reduced further, the bubbles 133 may grow in volume to form larger bubbles 133c, as shown in FIG. 3C, and new bubbles 133 may continue to be formed through nucleation. Some of the bubbles 133, 133c may coalesce to form even larger bubbles 133d, as shown in FIG. 3D.

The bubbles 133 may coalesce to form lumen-spanning bubbles 133e which span the entire diameter of a lumen of the channel 120, as shown in FIG. 3E. The formation of lumen-spanning bubbles 133e may be more likely in the regions of the mechanisms 330 due to a greater number or size of bubbles being formed and/or enhanced bubble coalescence.

When the pressure is increased, the liquid 130 is accelerated in a distal direction (i.e., towards the first or distal end 122 of the channel 120), as indicated by arrows 301 in FIG. 3F, and the bubbles 133 are compressed and reduce in volume, as shown in FIG. 3G.

When the bubbles 133 are compressed, they experience a sudden increase in pressure and density, and collapse (i.e., dissolve and/or condense) back into the liquid 130, as shown in FIG. 3A.

The mechanisms 330 may comprise any suitable means for enhancing, promoting, encouraging or increasing the likelihood of cavitation, bubble nucleation and/or bubble coalescence.

Figures 4, 5, 6:
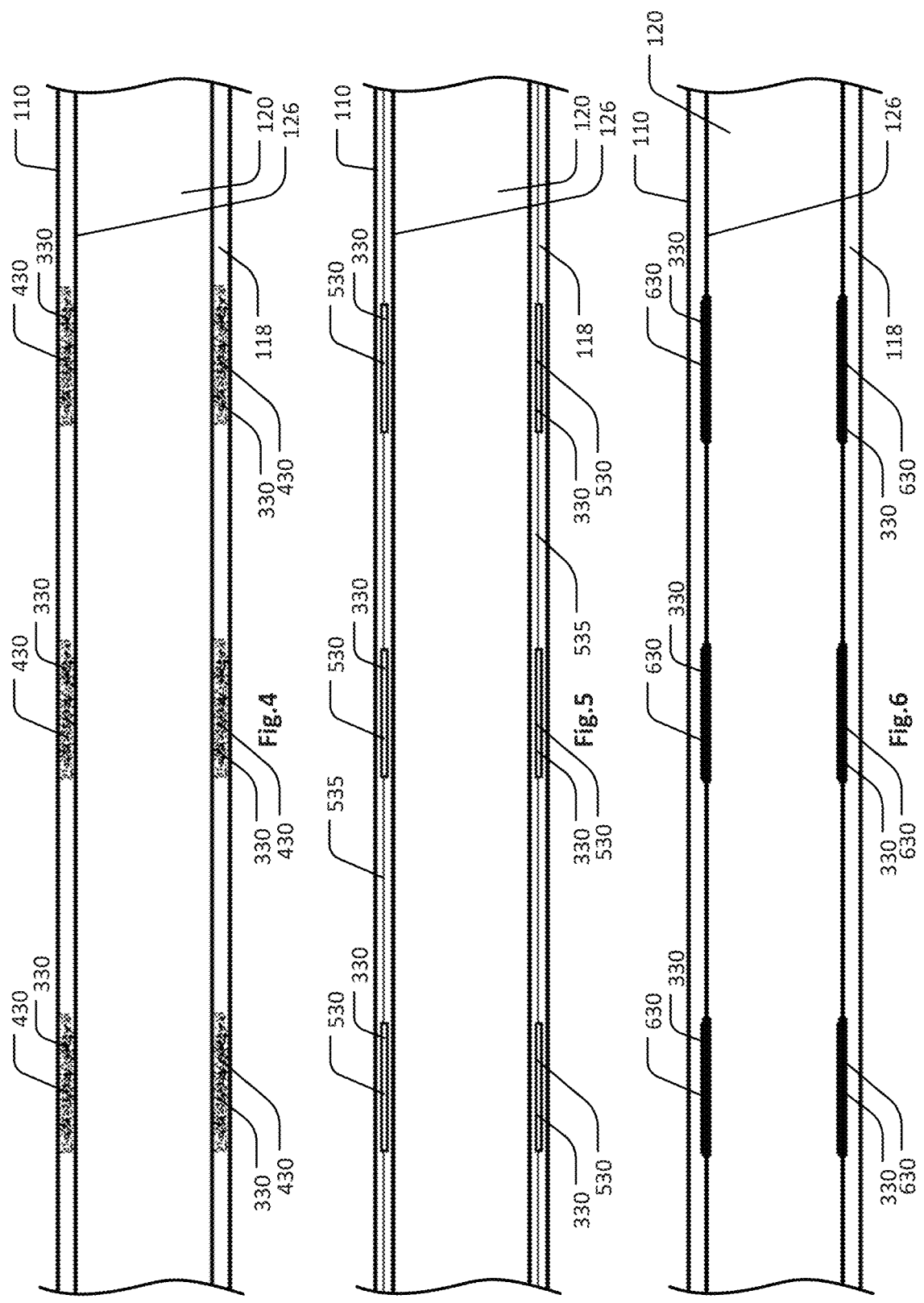
FIG. 4 is a longitudinal section of a portion of tube of a propulsion device illustrating mechanisms for promoting bubble nucleation and/or coalescence in certain regions within the tube, according to some embodiments.
FIG. 5 is a longitudinal section of a portion of tube of a propulsion device illustrating mechanisms for promoting bubble nucleation and/or coalescence in certain regions within the tube, according to some embodiments.
FIG. 6 is a longitudinal section of a portion of tube of a propulsion device illustrating mechanisms for promoting bubble nucleation and/or coalescence in certain regions within the tube, according to some embodiments.

Referring to FIG. 4, in some embodiments, the one or more mechanisms 330 may comprise a variation in a thermal conductivity and/or thermal mass of a wall 118 of the tube along the length of the channel 120. This variation in thermal conductivity and/or thermal mass could be achieved by including wall portions 430 at different locations along the length of the channel 120 comprising a material having a higher thermal conductivity and/or thermal mass than the rest of the wall 118. For example, in some embodiments, the wall 118 may be formed of an extruded polymer, and metal particles could be impregnated in certain portions of the wall 118 to create the wall portions 430 of relatively higher thermal mass and thermal conductivity.

The difference in thermal conductivity and/or thermal mass between the wall portions 430 and the rest of the wall 118 may result in a higher likelihood of cavitation and bubble nucleation in the region of the wall portions 430 compared with the rest of the channel 120.

In some embodiments, the thermal conductivity of the wall 118 may vary along the length of the channel over a range of about 0.25 $Wm^{-1}K^{-1}$ to 240 $Wm^{-1}K^{-1}$. In some embodiments, the thermal conductivity of the wall portions 430 may be higher than the rest of the wall 118 by a factor of at least 10, at least 100, at least 500, or at least 1000. For example, in some embodiments, the thermal conductivity of the wall portions 430 may be in the range of about 100 $Wm^{-1}K^{-1}$ to 300 $Wm^{-1}K^{-1}$, about 150 $Wm^{-1}K^{-1}$ to 250 $Wm^{-1}K^{-1}$, or about 200 $Wm^{-1}K^{-1}$, while the thermal conductivity of the rest of the wall 118 may be in the range of about 0.1 $Wm^{-1}K^{-1}$ to 10 $Wm^{-1}K^{-1}$, or about 0.5 $Wm^{-1}K^{-1}$ to 1 $Wm^{-1}K^{-1}$.

Referring to FIG. 5, in some embodiments, the one or more mechanisms 330 may comprise one or more acoustic transducers 530. The acoustic transducers 530 may be connected to a controller via one or more cables 535 and configured to emit acoustic energy with an amplitude and frequency which promotes cavitation, bubble nucleation and/or bubble coalescence.

The acoustic transducers 530 may be coupled to the external or internal surface of the tube 110, disposed outside of the 118 wall of the tube 110, or in some embodiments, may be disposed or embedded within the wall 118 of the tube 110. In some embodiments, the acoustic transducers 530 may comprise piezoelectric patch transducers.

An operating frequency of the acoustic transducers 530 may be in the range of about 1 kHz to 100 kHz or about 10 kHz to 25 kHz, for example. The operating frequency of the acoustic transducers 530 may be selected to be higher than the Blake threshold for the mechanical nucleation of gas bubbles of at least 1 micrometre in systems with a gas saturation coefficient approaching 1 (i.e fully saturated). The threshold increases with increasing frequency and decreasing gas saturation (for reference, see Acoustic cavitation prediction, R. E. Apfel, The Journal of the Acoustical Society of America 69, 1624 (1981).)

Acoustic insonation energy may be directed into a lumen of the channel by the acoustic transducers 530 to promote, enhance or assist in inducing cavitation in the liquid 130. In some embodiments, the characteristics of the insonation field may comprise: a pressure variation in the range of about 10 MPa to 100 Mpa, a pulse duration in the range of about 0.2 ms 10 ms, and a total power in the range of about 10 mW to 100 mW, for example. In some embodiments, the acoustic transducers 530 may be operated with a pressure of about 100 kPa, a displacement of about 25 μm and a frequency of about 21 kHz.

In some embodiments, the mechanisms 330 may comprise one or more lasers configured to induce cavitation in the liquid 130. For example, in some embodiments, the mechanisms 330 may comprise microdiode laser modules embedded in the wall 118 of the tube 110. The laser modules may be activated in a pulse of 10 ms to 20 ms duration to co-inside with the low pressure phase of the pressure cycle, to promote, enhance or assist in inducing nucleation of gas bubbles 133.

In some embodiments, the mechanisms 330 may comprise one or more pairs of electrical conductors disposed within the lumen of the channel 120 and arranged with a close separation in the range of about 0.1 mm to 0.5 mm, such that an electrical current can discharge from one conductor to the other through the liquid 130 causing ionisation of the liquid 130 and subsequent gas nucleation. The conductive pairs may be arranged in a circular configuration and imbedded in the wall of the non-conductive polymer tube. The conductive pairs may be connected to an electrical power source via conductive wires running along the length of the tube 110. The power source may comprise a high capacity, high voltage, low current discharge circuit which can be timed to discharge at the lowest point of the pressure cycle produced by the pressure actuator 140. The supplied voltage may be in the range of about 100V to 200V. The current may be in the range of about 1 mA to 10 mA.

Referring to FIG. 6, in some embodiments, the one or more mechanisms 330 may comprise a surface variation 630 on the internal surface 126 of the tube 110. That is, a surface variation portion 630 of the internal surface 126, which is different to the rest of the internal surface 126 and configured to promote or encourage bubble nucleation.

In some embodiments, the surface variation 630 may comprise a coating applied to part of the internal surface 126 of the tube 110. In some embodiments, the surface variation 630 may comprise a coating of a catalytic material, such as octadecyltrichlorosilane (for promoting $CO_2$ nucleation) or other similar compounds, for example. In some embodiments, the surface variation 630 may comprise a hydrophobic coating, such as silane (silicone hydride) compounds, Parylene C, or flouropolymers such as PTFE (Teflon™), manganese oxide polystyrene (MnO2/PS), nano-composite zinc oxide polystyrene (ZnO/PS), nano-composite precipitated calcium carbonate or fluorinated acrylate oligomers, for example.

In some embodiments, the rest of the internal surface 126 may be formed of or coated with a hydrophilic material, such as urethane, acrylic, polyvinylpyrrolidone (PVP), polyethylene oxide, combinations of hydroxyethylmethacrylate, or acrylamides, for example, or another material suitable for discouraging bubble nucleation on the rest of the internal surface 126 (i.e. away from the surface variations 630).

In some embodiments, the surface variation 630 may comprise a topographical variation. Relatively small topographical variations (e.g., at length scales in the order of 1 μm-100 μm) may provide nucleation sites to encourage or promote bubble nucleation and growth. For example, the topographical variation may comprise a change in surface roughness, a microporous surface, a scratched or pitted surface, a plurality of protrusions, projecting fibres, nanotubes, pits, channels, ridges, fins, recesses, cavities or other geometrical variation. The topographical variations may be formed by moulding, scratching, cutting, knurling, etching, abrasion, or impression, for example. In some embodiments, porous particulates such as ceramics may be embedded in the wall 118 of the tube 110 at the inner surface 126 to provide nucleation sites.

In some embodiments, the topographical variation may extend across the entire internal surface 126 of the tube 110. In some embodiments, the tube 110 may be formed with the topographical variation extending across the entire internal surface 126, and then certain portions of the internal surface 126 may be smoothed (for example, with a polymer coating), leaving the exposed/unsmoothed portions of the topographical variation to form the surface variations 630. For example, the wall 118 of the tube 110 may be formed of a porous material, and then certain portions of the inner surface 126 may be sealed leaving the exposed/unsealed portions of the inner surface 126 to form the surface variations 630.

The surface variations 630 may comprise any suitable topographical variations for a given application. A number of suitable topographical variations are described below.

In some embodiments, the topographical variation may define a plurality of V-shaped channels. The V-shaped channels may be aligned in parallel with each other, or may be randomly oriented and intersect each other.

A characteristic angle of the V-shaped channels (i.e., the angle of the apex of the V-shape) may be in the range of about 10° to 90°, about 30° to 60°, or about 40° to 50°, for example. An average width of the V-shaped channels may be in the range of about 1 μm to 10 μm, or about 2 μm to 4 μm, for example. An average depth of the V-shaped channels may be in the range of about 1 μm to 10 μm, or about 2 μm to 4 μm, for example.

Figures 7, 8A, 8B, 8C, 8D, 8E, 9:
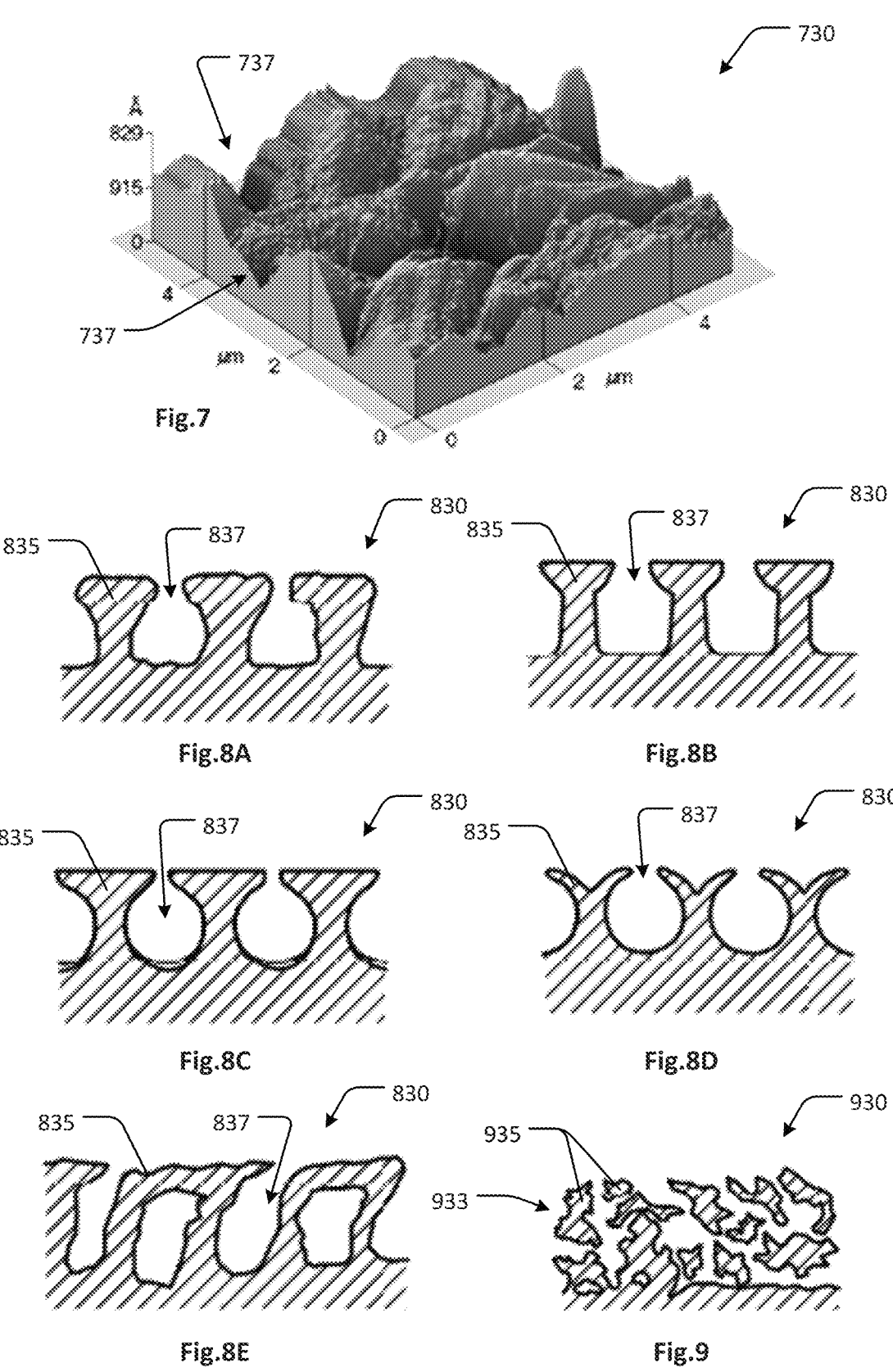
FIG. 7 is an illustration of a topographical surface variation for promoting bubble nucleation, according to some embodiments.
FIGS. 8A to 8E show a series of illustrations of different types of protrusions for promoting bubble nucleation, according to some embodiments.
FIG. 9 is an illustration of a porous surface for promoting bubble nucleation, according to some embodiments.

Referring to FIG. 7, in some embodiments, a surface variation 730 may comprise a partially randomised pattern of intersecting V-shaped channels 737. This may be achieved by abrasion using Diamond particulates with a nominal size of 2 μm. The Diamond particulates may have sharp V-shaped vertices and may be sintered on to a metal rod for rotary application to the internal surface 126. The metal rod may be applied to the internal surface 126 with a rotary oscillation to produce the surface variations 730. An Atomic Force micrograph of a typical random V-shaped scratch pattern achieved using this method is shown in FIG. 7.

In some embodiments, the topographical variation may define a plurality of conical pits. The conical pits may be arranged randomly or in a periodic array.

A characteristic angle of the conical pits (i.e., the angle of the apex of the conical pits) may be in the range of about 10° to 90°, about 30° to 60°, or about 40° to 50°, for example. An average width of the conical pits may be in the range of about 1 μm to 10 μm, or about 2 μm to 4 μm, for example. An average depth of the conical pits may be in the range of about 1 μm to 10 μm, or about 2 μm to 4 μm, for example.

In some embodiments, the topographical variation may define a plurality of protrusions. The protrusions may define any suitable shape and, in some embodiments, may define a plurality of different shapes. The protrusions may be arranged randomly or in a periodic array.

An average height of the protrusions may be in the range of about 0.1 μm to 1 mm, about 1 μm to 500 μm, or about 10 μm to 100 μm, for example. An average width of the protrusions may be in the range of about 0.1 μm to 500 μm, about 0.5 μm to 100 μm, or about 1 μm to 10 μm, for example. An average distance between adjacent protrusions may be in the range of about 0.1 μm to 500 μm, about 0.5 μm to 100 μm, or about 1 μm to 10 μm, for example.

Referring to FIGS. 8A to 8E, some examples of surface variations 830 are shown according to some embodiments. The surface variations 830 each define a plurality of protrusions 835. In some embodiments, the protrusions 835 may define fins or ridges 835 separated by channels 837.

In some embodiments, the protrusions 835 may comprise nanowires or hollow nanotubes which may be formed of materials such as carbon or silicon, for example. For nanowire, the width of the protrusions 835 may be in the range of about 10 nm to 500 nm, about to 300 nm, or about 100 nm to 200 nm; the length or height of the protrusions 835 may be in the range of about 0.1 μm to 100 μm, about 1 μm to 50 μm, or about 10 μm to 20 μm; and the average spacing between protrusions 835 may be in the range of about 10 nm to 10 μm, about 10 nm to 100 nm, or about 100 nm to 1 μm, for example. For nanotubes, the width of the protrusions 835 may be in the range of about 10 nm to 100 nm, about 10 nm to 50 nm, or about to 40 nm; the length or height of the protrusions 835 may be in the range of about 1 μm to 50 μm, about 5 μm to 30 μm, or about 10 μm to 20 μm; the pore size (or internal diameter) of the protrusions 835 may be in the range of about 1 μm to 40 μm, about 5 μm to 30 μm, or about 10 μm to 20 μm; and the average spacing between protrusions 835 may be in the range of about 10 nm to 10 μm, about 10 nm to 100 nm, or about 100 nm to 1 μm, for example.

In some embodiments, the topographical variation may define a porous surface, such as a foam, sintered material or other porous material, for example. An average pore size of the porous surface may be in the range of about 10 nm to 200 μm, about 20 nm to 250 nm, about 50 nm to 150 nm, about 10 μm to about 200 μm, or about 50 μm to about 100 μm, for example. The porous surface may comprise a layer of porous material. The thickness of the porous layer may be in the range of about 10 μm to 1 mm, or about 50 μm to 100 μm, for example.

Referring to FIG. 9, a surface variation 930 comprising a porous layer 933 is shown according to some embodiments. The porous layer 933 may be formed of sintered particles 935 with diameters ranging from about 10 μm to about 100 μm, for example.

In some embodiments, the topographical variation may have a surface roughness in the range of about 0.1 μm to 500 μm, about 0.5 μm to 100 μm, or about 1 μm to 10 μm, for example.

In some embodiments, one or more additives may be included in the liquid 13- to promote cavitation, bubble nucleation and/or bubble coalescence. For example, additives may be included to alter the density, viscosity, pH-level, gas solubility, coalescence characteristics or surface tension of the liquid 130.

The solubility and coalescence characteristics of each fluid gas combination may be dependent on factors which may be controlled, such as temperature and pH. In the case of $CO_2$, it is thought that the pH of the solution should ideally be adjusted to be between 6 and 6.5 for optimum effect. If the pH is above 6.5 it may be difficult to induce bubble nucleation due to the high solubility of the gas in water. In some embodiments, where $CO_2$ is used as the gas, the pH of the solution may be decreased to a level between 6 and 6.5 with the addition of acetic acid producing to promote nucleation and coalescence of $CO_2$ bubbles in the liquid.

In some applications, the mechanical work of the pressure actuator 140 acting on the liquid 130 may produce heating of the liquid 130, which may decrease the solubility of the gas 133 in the liquid 130. In some embodiments, the propulsion device 100 may include a heat sink (not shown) to draw excess heat away from the liquid 130. For example, the heat sink may comprise a metal heat sink disposed at or near the proximal end 114 of the tube 110, which may be disposed within or adjacent to the pressure actuator 140. The heat sink may be cooled by air convection, refrigeration, or radiation.

In some embodiments, the thermal conductivity of the liquid 130 may be sufficient for heat to be transferred through the liquid 130 along the tube 110 to the heat sink. In some embodiments, salts such as Potassium Formate may be added to water to increase the thermal conductivity and density of the liquid 130 without significantly increasing the viscosity or boiling point.

In some embodiments, the thermal mass and conductivity of the tube 110 itself may be sufficient for heat to be transferred along the tube 110 to the heat sink. In some embodiments, the tube wall 118 may comprise one or more heat conductors, such as a metallic film or wire, to transfer heat along the tube 110 to the heat sink.

In some embodiments, the liquid 130 may comprise a particularly dense liquid and/or one or more additives may be included in the liquid 130 to increase the density or inertia of the liquid 130 in order to increase the momentum developed when the liquid 130 is accelerated and thus to increase the momentum transferred to the tube 110 to progress the tube 110 along the passage.

In some embodiments, such as for medical use, the liquid 130 may comprise water combined with one or more additives, such as: ethanol to reduce surface tension and viscosity; citric acid or acetic acid to reduce the pH-level; or salts such as sodium chloride to increase the density.

In some embodiments, the internal surface 126 of the tube 110 may define a relatively large scale topographical variation (for example, with length scales in the range of about 5% to 10% of the internal diameter of the tube 110) configured to enhance momentum transfer from the liquid 130 to the tube 110 during the sudden pressure increase.

Figures 10A, 10B, 10C:
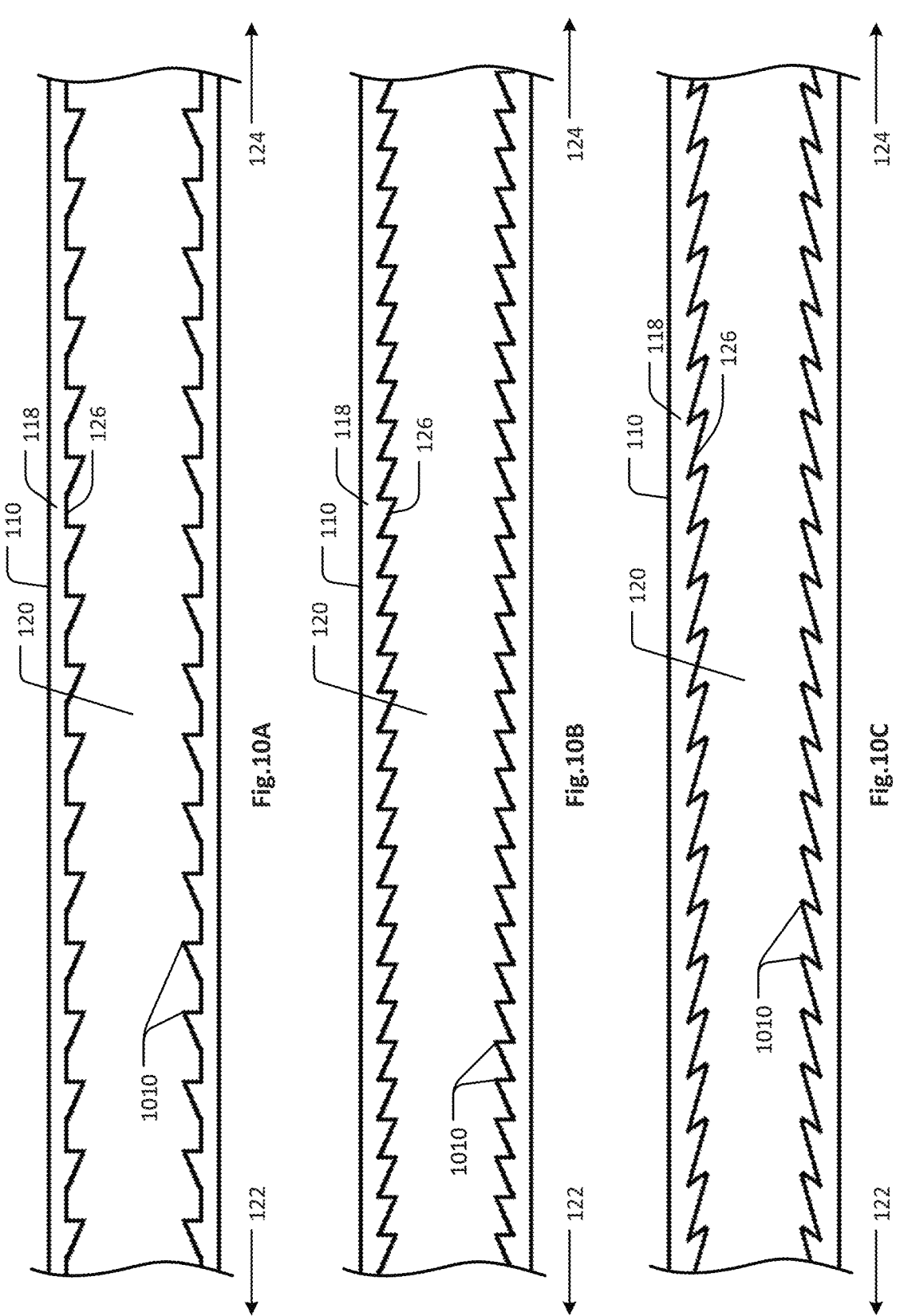
FIGS. 10A to 10C show a series of illustrations of different types of large scale topographical surface variations for enhancing momentum transfer between the liquid and the tube, according to some embodiments.

Referring to FIGS. 10A to 10C, segments of tube 110 are shown illustrating some examples of large scale topographical variations defined by the internal surface 126, according to some embodiments. The internal surface 126 may define a plurality of periodic annular ridges 1010 swept back in a proximal direction (towards the second or proximal end 124 of the channel 120). The ridges 1010 appear as a swept fir tree pattern, or proximally swept teeth in cross-section as shown in FIGS. 10A to 10C.

The proximally swept annular ridges 1010 may provide a fluid diode effect, whereby there is a greater resistance to fluid flow in the distal direction and relatively less resistance to fluid flow in the proximal direction. This effect may enhance momentum transfer from the liquid 130 to the tube 110 during the sudden pressure increase.

In some embodiments, the annular ridges 1010 may not be proximally swept, and a fluid diode effect may be achieved with a different type of topographical variation or, in some embodiments, not at all.

As described above, when the channel 120 accommodates a volume of liquid 130 and a separate volume of gas 133 in an initial or rest state, the pressure actuator 140 may be configured to increase the channel pressure to dissolve the gas 133 into the liquid 130 (this may be referred to as a pressure increase phase), and subsequently decrease the channel pressure to induce nucleation and cavitation of gas bubbles 133 in the liquid 130 (this may be referred to as a pressure decrease phase). Alternatively, when the channel 120 accommodates only the liquid 130 in the initial or rest state, the pressure actuator 140 may be configured to decrease the channel pressure to induce nucleation and cavitation of gas bubbles 133 in the liquid 130 (the pressure decrease phase), and subsequently increase the channel pressure to collapse the gas bubbles 133 (through condensation or dissolution) into the liquid 130 (the pressure increase phase).

In some embodiments, the pressure increase phase may be substantially similar in duration to the pressure decrease phase. In some embodiments, the duration of the pressure increase phase may be significantly shorter than the duration of the pressure decrease phase.

In some embodiments, the pressure actuator 140 may be configured to increase the pressure over a period of time which is between about 1% and 50% of a period of time over which the pressure is reduced, optionally between about 5% and 30%, optionally between about 10% and 20%, for example.

As described above, the pressure actuator 140 may comprise any suitable apparatus for varying the channel pressure in the manner described. In some embodiments, the pressure actuator 140 may comprise a flexible diaphragm with a mechanism configured to deflect or deform the diaphragm to change the volume of the system and control the channel pressure. In some embodiments, the pressure actuator 140 may comprise a reciprocating piston driven by a motor, such as an electric motor or linear motor, for example.

Figure 11:
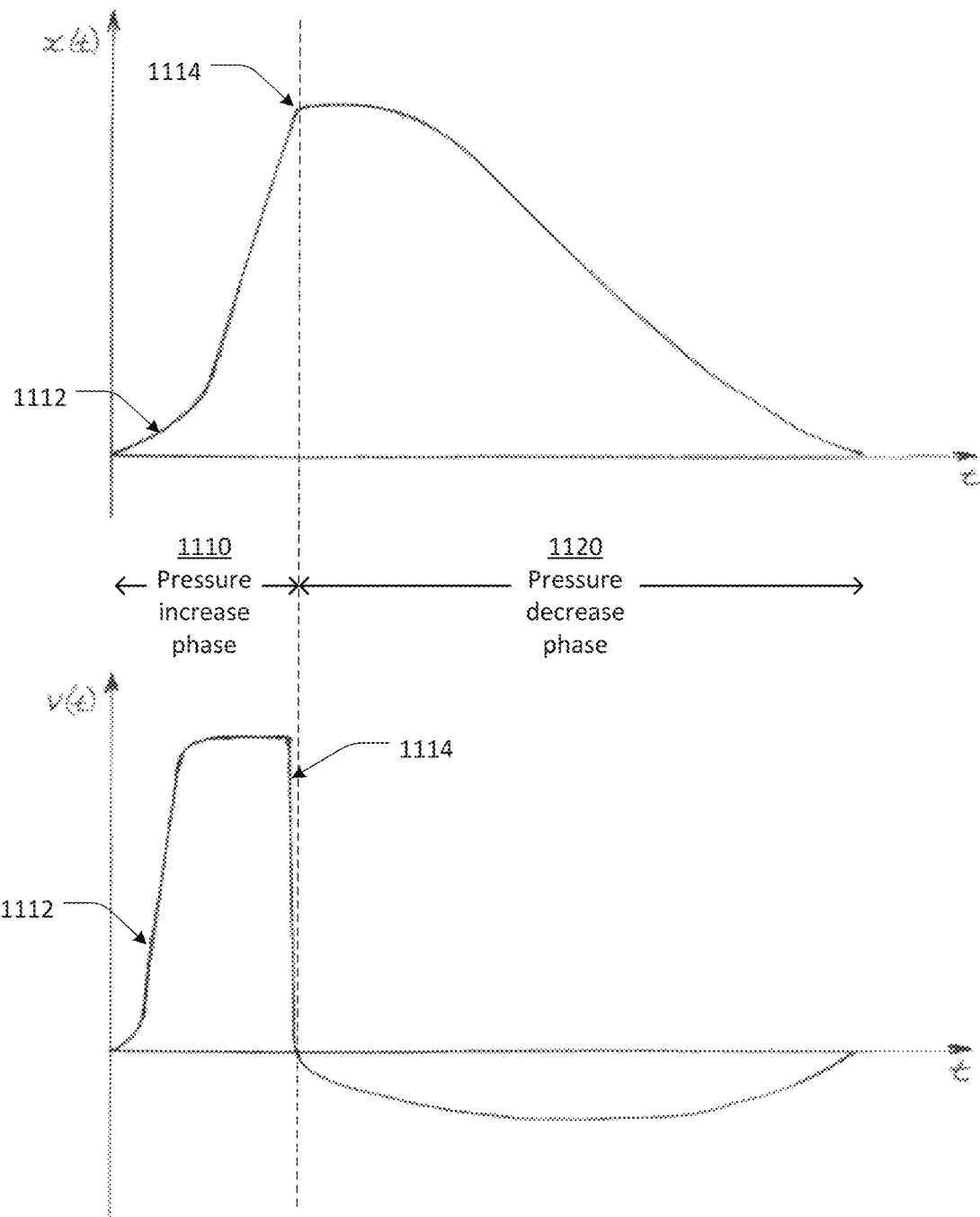
FIG. 11 shows exemplary displacement and velocity profiles illustrating the movement of a piston of a pressure actuator, according to some embodiments.

Referring to FIG. 11, an exemplary displacement profile x(t) and corresponding velocity profile v(t) are shown illustrating the movement of the pressure actuator 140, in the form of a piston, over time, according to some embodiments.

The displacement and velocity profiles show a pressure increase phase 1110 followed by a pressure decrease phase 1120. During the pressure increase phase 1110 (corresponding to a compression stroke of the piston), the piston undergoes a rapid acceleration 1112 which is made possible by the highly compressible nature of the gas bubbles 133.

Once the gas bubbles 133 collapse back into the liquid 130, there is a sudden deceleration 1114 of the piston due to the relatively incompressible nature of the liquid 130 (i.e., greatly less compressible than the gas 133). The sudden deceleration 1114 of the piston and liquid 130 results in a large impulse and transfer of momentum from the liquid 130 to the tube 110 and a consequent propulsive effect which acts to progress the tube 110 along the passage 103.

After the deceleration 1114 of the piston, once the channel pressure has reached a maximum the pressure decrease phase 1120 begins as the piston is withdrawn. The withdrawal stroke (pressure decrease phase 1120) may be significantly slower than the compression stroke (pressure increase phase 1110) due to the time required for nucleation and cavitation of the gas bubbles 133 to occur. The channel pressure is then decreased to a minimum. The movement of the piston may then be repeated in a similar manner to repeat the pressure variation cycle.

The pressure actuator 140 may be configured to repeatedly increase and decrease the channel pressure to impart momentum to the tube 110 with multiple impulses, each impulse being associated with corresponding pressure increase phases. In some embodiments, the channel pressure may be varied by the pressure actuator 140 in a periodic or cyclic manner with a repeating pressure cycle (i.e., pressure increase followed by pressure decrease). In some embodiments, the pressure actuator 140 may be configured to vary the channel pressure according to a repeating pressure cycle with a frequency in the range of about 0.1 Hz to 10 Hz, about 0.5 Hz to 5 Hz, about 0.5 Hz to 1.5 Hz, about 2 Hz to 4 Hz, or about 3 Hz, for example.

In some embodiments, the pressure actuator 140 may be configured to operate in a reverse cycle to adjust the channel pressure to impart a reverse impulse to the tube 110 to move the instrument in a proximal direction. This reverse pressure cycle may be used to withdraw the instrument from the passage.

Referring to FIG. 12, an exemplary pressure/time profile is shown, according to some embodiments, illustrating the changes in channel pressure required to compress the gas bubbles 133 into the liquid 130 when the pressure is increased, and subsequently induce cavitation of gas bubbles 133 in the liquid 130 when the pressure is reduced. The pressure scale is shown in kilopascals (kPa) above atmospheric pressure and the time scale is shown in seconds. The channel pressure is reduced gradually over a period of about 0.3 s, and then suddenly increased over a period of about 0.05 s. This pressurisation cycle is repeated at a frequency of about 3 Hz.

As discussed previously, in some embodiments, it may be desirable for the channel 120 to be relatively small in order to increase the likelihood of spanning bubbles 133e forming before compression. The internal diameter of the channel 120 may be in the range of 0.1 mm to 10 mm, 0.1 mm to 1 mm, 0.1 mm to 0.5 mm, 1 mm to 7 mm, or 2 mm to 5 mm, for example. In some embodiments, the propulsion device 100 may comprise a plurality of the tubes 110 extending side by side as illustrated by the cross-sections of example tube configurations shown in FIGS. 13A and 13B.

In some embodiments, the tubes 110 may be arranged around an instrument channel 1301 configured to receive a probe such as an endoscope, for example as illustrated in FIG. 13B. In some embodiments, the tubes 110 may be arranged in a bundle for insertion into a lumen of a probe such as an endoscope, for example as illustrated in FIG. 13A. In some embodiments, the tubes 110 may be integrally formed as part of a probe such as an endoscope, with instrument channels (e.g. video tract, lighting, irrigation, suction, steering, biopsy and other instrument channels) extending alongside the tubes 110.

In some embodiments, the propulsion device 100 may comprise a first tube 110 within a second tube 110, with the liquid 130 and gas 133 contained in an annular channel 120 defined between the two tubes 110. An inner lumen of the first tube 110 may also contain liquid 130 and gas 133, or alternatively, in some embodiments, the inner lumen of the first tube 110 may define an instrument channel.

The tube 110 or tubes 110 may be formed of a flexible material with sufficient strength and stiffness to withstand the expected forces for a given application. For medical applications, some suitable materials may comprise: high to ultra-high molecular weight polyethylene or other biocompatible polymers, for example. In some embodiments, the tube 110 or tubes 110 may be formed of composite materials, such as a polyethylene spiral with polyurethane and silicone elastomer coatings, for example.

The dimensions of the tubes 110 may vary for different applications. For example, for a medical endoscope, such as a gastro-intestinal endoscope, a single tube propulsion device may comprise a tube 110 with an external diameter of 8 mm and an internal diameter of 6 mm, or an external diameter of 6 mm and an internal diameter of 4.5 mm, whereas a multi-tube propulsion device may comprise 4 tubes 110, each having an external diameter of 3 mm and an internal diameter of 2 mm. In some embodiments, the tube 110 of a single tube propulsion device 100 or the tubes 110 of a multi-tube propulsion device 100 may have an internal diameter in the range of 1 mm to 5 mm, for example, and an external diameter in the range of 0.5 mm to 15 mm, 1 mm to 10 mm, 2 mm to 8 mm or 4 mm to 6 mm, for example. The lengths of medical endoscopes are typically in the range of about 1 m to 5 m, or about 3 m to 4 m, for example. In some embodiments, such as for gastro-intestinal endoscopy, the tube(s) 110 may have a length in the range of 3 m to 4 m, 1 m to 5 m, or even greater than 5 m, such as 5 m to 15 m, or 7 m to 9 m, for veterinary applications, for example. In some embodiments, such as for arterial endoscopy, the tube(s) may have a length in the range of 0.5 m to 2 m, 0.7 m to 1.5 m or 0.9 m to 1.2 m, for example. In some embodiments, such as for industrial endoscopes, the dimensions of the tubes may be much larger.

Figure 14:
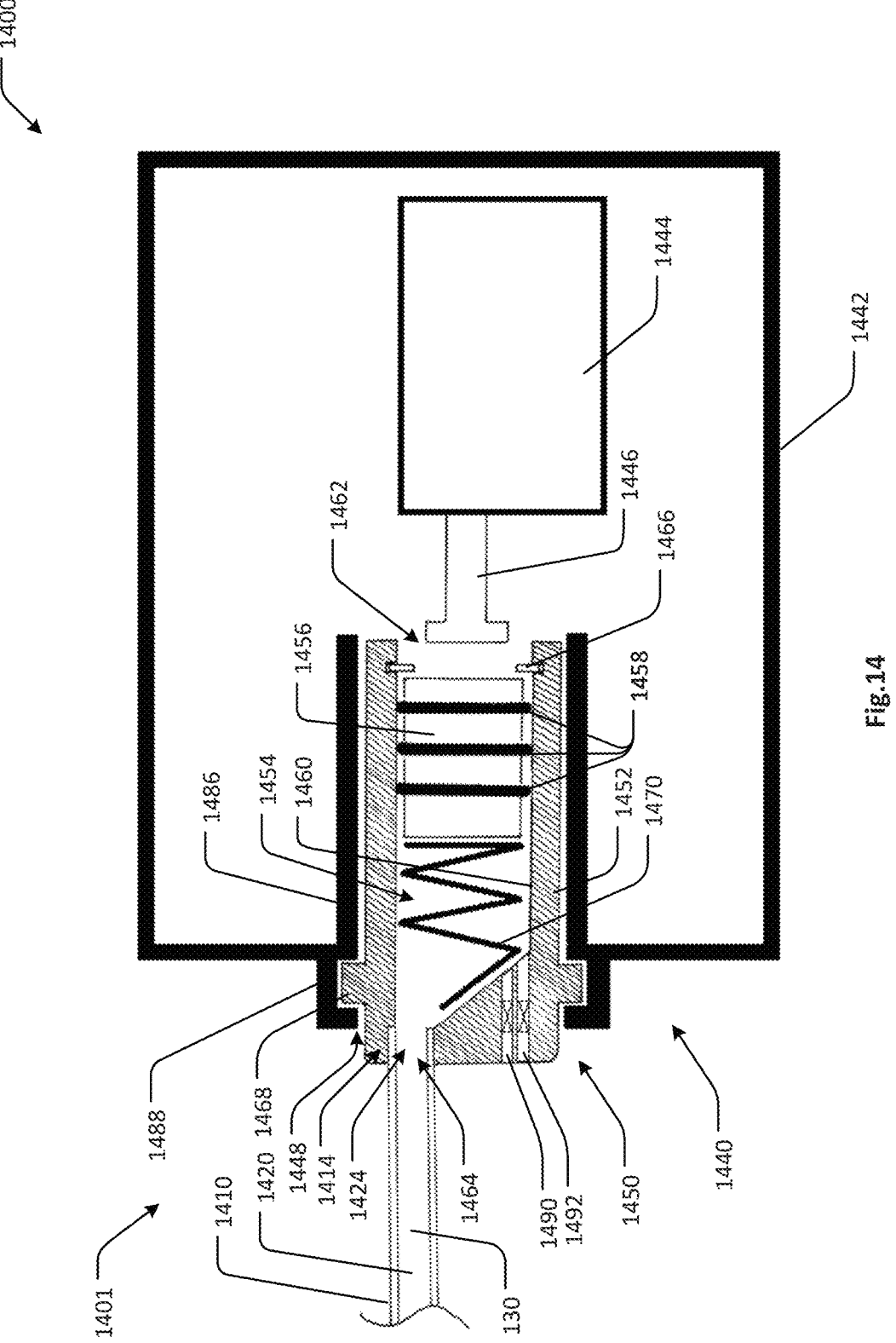
FIG. 14 shows a schematic diagram of part of a propulsion device with a removable tube and piston assembly, according to some embodiments.

For medical applications, it will usually be important for the propulsion device 100 to be sterile. To that end, it may be desirable for at least part of the device 100 to comprise a disposable component which can be provided in a sterile package and discarded after use. Referring to FIG. 14, a propulsion device 1400 is shown according to some embodiments. The propulsion device 1400 comprises generally similar features to those described in relation to propulsion device 100 and are referred to with like numbers. A pressure actuator 1440 and proximal end 1414 of a tube 1410 defining a channel 1420 are shown. It will be understood that the tube 1410 extends to a distal end (not shown) as described in relation to the propulsion device 100 of FIG. 1. The tube 1410 may be referred to as a propulsion tube, and may comprise similar features to tube 110 described above. In some embodiments, tube 1410 may comprise tube 110, or a bundle of tubes 110 as described in relation to FIG. 13A or 13B.

The pressure actuator 1440 comprises a housing 1442, a driving mechanism 1444 (in the form of a motor), an actuation rod 1446 and a socket 1448 defined in a side of the housing 1442. The pressure actuator 1440 further comprises a piston assembly 1450 comprising a body 1452 defining a cylinder 1454, a piston 1456 disposed in the cylinder, and a piston seal 158 to seal the piston 1456 against an internal bore 1460 of the cylinder 1454. The piston 1456 and cylinder 1454 act together to form a piston pump. However, in some embodiments, a different type of pump or compressor may be used to adjust the channel pressure in the tube 1410, for example, a diaphragm pump, as described below in relation to FIG. 17.

The piston assembly 1450 is attached to the tube 1410 to form a tube unit 1401. The tube unit 1401 may be manufactured and filled with a predetermined mass of liquid 130 and a predetermined mass of gas 133 sealed within the channel 1420 of the tube 1410 at a predetermined pressure. The tube unit 1401 may then be packaged and sterilised separately from the housing 1442 (including the socket 1448 and driving mechanism 1444) so that the housing 1442 can be resterilised and reused, while the tube unit 1401 can be manufactured and sterilised as a disposable unit to be discarded after use.

This arrangement may make it easier to sterilise the fluid 130, 133 and tube unit 1401 together rather than having to fill the tube 1410 with sterile fluid 130, 133 in a sterile environment such as an operating theatre.

The piston assembly 1450 is removably coupled to the housing 1442 (i.e., removable from the socket 1448). The socket 1448 may comprise an internal cylindrical wall 1486 that helps define the socket 1448 and accommodate the piston assembly 1450 in the socket 1448.

The body 1452 defines a first opening 1462 and a second opening 1464 with the cylinder 1454 defining an open passage between the first and second openings 1462, 1464. The proximal end 1414 of the tube 1410 is connected to the body 1452 of the piston assembly 1450 at the second opening 1464, such that the channel 1420 is in fluid communication with the cylinder 1454. The internal diameter or bore of the cylinder 1454 may be significantly larger than the internal diameter of the tube 1410 so that a relatively shorter stroke length is required to affect the desired pressure changes in the tube 1410. For example, the ratio between the internal diameters of the tube 1410 and the cylinder 1454 may be in the range of 0.01 to 0.5, 0.05 to 0.4, 0.1 to 0.3, or 0.1 to 0.2.

The internal diameter of the cylinder 1454 may gradually taper down to the internal diameter of the tube 1410 at the second opening 1464. In some embodiments, the second opening 1464 may be offset from a central axis of the body 1452, and may be disposed at or near a top of the cylinder 1454 when the pressure actuator 1440 is disposed in a horizontal configuration. This may reduce the likelihood of gas bubbles, which may be formed in the cylinder 1454 during cavitation, being trapped in the cylinder, and instead, allow the bubbles to rise up towards the second opening 1464 and into the tube 1410 due to gravity.

The pressure actuator 1440 is configured to move the piston 1456 back and forth along the length of the cylinder 1454 to adjust the channel pressure, such as by varying the channel pressure in the tube 1410. A compression stroke, or pressure increase stroke, moves the piston 1456 towards the tube 1410 and pushes fluid from the cylinder 1454 and into the tube 1410, thereby increasing the channel pressure in the tube 1410. A return stroke, or withdrawal or pressure decrease stroke, moves the piston 1456 away from the tube 1410 and allows fluid to flow back into the cylinder 1454 from the tube 1410, thereby decreasing the channel pressure in the tube 1410.

The motor 1444 and actuation rod 1446 are disposed in the housing 1442, such that when the piston assembly 1450 is disposed in the socket 1448, the actuation rod 1446 is aligned with the first opening 1462 of the body 1452 and can pass through the first opening 1462 to contact and move the piston 1456 within the cylinder 1454. In some embodiments, the channel pressure within the tube 1410 may be sufficient to move the piston 1456 through the return stroke when the actuation rod 1446 is withdrawn from the cylinder 1454. In some embodiments, the piston assembly 1450 may further comprise a biasing member 1470, such as a spring, to bias the piston 1456 against the actuation rod 1446 and/or away from the tube 1410, such that the piston 1456 is pushed back through the return stroke by the biasing member 1470 when the actuation rod 1446 is withdrawn from the cylinder 1454. For example, the biasing member 1470 may comprise a stainless steel spring and/or a helical spring. In some embodiments, the actuation rod 1446 may be removably couplable to the piston 1456 itself to allow the actuation rod 1446 to pull the piston 1456 back as well as pushing the piston 1456 forward.

The piston assembly 1450 may further comprise a locking ring 1466 to restrict the piston 1456 from being removed from the cylinder 1454 through the first opening 1462. In some embodiments, the driving mechanism 1444 may comprise one or more electromagnets configured to drive the piston 1456 directly rather than via a motor and actuation rod.

The body 1452 may further define one or more locking lugs 1468 configured to engage the socket 1448 to couple the piston assembly 1450 to the housing 1442. The socket 1448 may also comprise one or more external flanges 1488 configured to engage the lugs 1468 to secure the piston assembly 1450 in the socket 1448. In this way, the piston assembly 1450 is configured to be removably coupled to the housing 1442, such that the piston assembly 1450 and tube 1410 can be manufactured together as a single disposable tube unit, while the housing 1442 and motor 1444 can be reused with a new tube unit for each new operation. The locking lugs 1468 may alternatively be referred to as tabs or radial projections, for example.

The tube unit may be assembled with liquid 130 and gas 133 disposed in the channel 1420 (either at atmospheric pressure or at a higher pressure depending on the application) and connected to the piston assembly 1450 to seal liquid 130 and gas 133 within the tube unit. In some embodiments, the body 1452 may be fixed to the proximal 1414 end of the tube 1410 and the piston 1456 subsequently placed in the cylinder 1454 and locked in with the locking ring 1466 to seal the liquid 130 and gas 133 in the channel 1420 and cylinder 1454. The seal 1458 may comprise one or more gaskets such as o-rings, which may be seated in one or more corresponding gasket seats defined in the piston 1456, or alternatively in the inner surface of the cylinder 1454.

In some embodiments, the body 1452 of the piston assembly 1450 may include an inlet valve 1490 for filling cylinder 1454 and the channel 1420 of the tube 1410 with a predetermined mass of a selected liquid 130 and a predetermined mass of a selected gas 133. The body 1452 may also include an outlet valve 1492 to allow air to be released from the channel 1420 and cylinder 1454 while they are being filled with the liquid 130 and gas 133.

The valves 1490, 1492 may be located at one end of the body 1452 near the second opening and may be configured to maintain pressure within the cylinder 1454 and channel 1420. In some embodiments, the valves 1490, 1492 may comprise spring plunger valves. The inlet valve 1490 may be located relatively nearer the second opening 1464 and the outlet valve 1492 may be located relatively farther from the second opening 1464, as shown in FIG. 14.

To fill the tube unit 1401 with the gas 133 and liquid 130, the body 1452 may be held upside down, or arranged with the valves 1490, 1492 disposed above the second opening, with most or substantially all of the volume of the channel 1420 and cylinder 1454 at a lower level than the outlet valve 1492. This is to encourage excess air to rise towards the outlet valve 1492 when the channel 1420 and cylinder 1454 are being filled with the liquid 130. The air may be sucked from the outlet valve 1492 via a vacuum line or other suction.

In some cases, the liquid 130 and gas 133 may be mixed together in a pressure vessel, such that the gas 133 is fully dissolved in the liquid 130 in a saturated solution, in which case the gas/liquid solution can be introduced to the tube unit 1401 via the inlet valve 1490 as the air is removed via the outlet valve 1492. If the gas 133 and liquid 130 are to be introduced separately, it may be preferable to first remove as much air as possible from the channel 1420 and cylinder 1454 via the outlet valve 1492; before injecting the liquid 130 into the channel 1420 and cylinder 1454 via the inlet valve 1490; removing any remaining air via the outlet valve 1492; and then injecting the gas 133 into the channel 1420 and cylinder 1454 via the inlet valve 1492.

Alternatively, the tube 1410 could be formed with an open distal end; the liquid 130 and gas 133 could be drawn along the channel 1420 and into the cylinder 1454 as the air is withdrawn from the cylinder 1454; and then the distal end of the tube 1410 could be closed with a plug and steel swage to hold the plug in the channel 1420 and seal the tube 1410. However, it may be preferable to form the tube 1410 with a closed distal end to avoid having to close it with a plug or other means.

Once the tube unit is fully assembled with the liquid 130 and gas 133 sealed inside the channel 1420 and cylinder 1454, the tube unit may be packaged and sterilised with gamma radiation, for example. Together, the tube 1410 and piston assembly 1450 may define a sealed vessel containing a selected mass of liquid 130 and a selected mass of gas 133. In some embodiments, a gas tight closure may be fitted to the body 1452 of the piston assembly 1450 during packaging to close the first opening 1462 of the cylinder 1454 and to assist in maintaining a selected tube channel pressure until use. The body 1452 may comprise an engaging portion (not shown) defining one or more recesses, notches or projections to engage the closure and form a gas tight seal.

Figure 17:
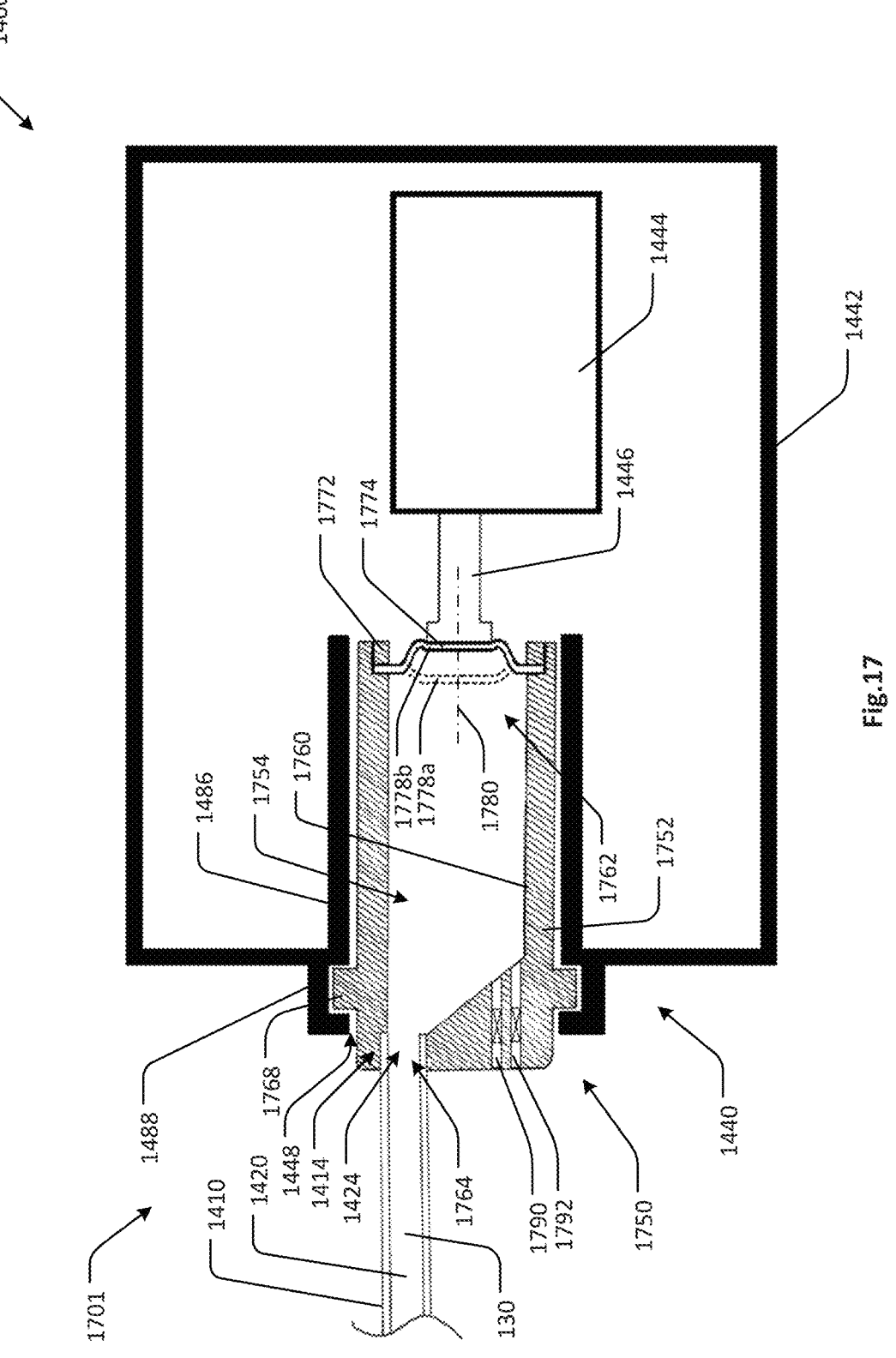
FIG. 17 shows a propulsion device with an alternative tube unit according to some embodiments.

In some embodiments, the pressure actuator 1440 may comprise a diaphragm pump instead of a piston pump to control the channel pressure in the tube 1410. Referring to FIG. 17, the propulsion device 1400 is shown with an alternative tube unit 1701, comprising a diaphragm pump assembly 1750 instead of the piston assembly 1450 described above. In all other respects, the tube unit 1701 may be substantially similar to the tube unit 1401 described above with similar features indicated with like reference numerals.

The diaphragm pump assembly 1750 comprises a body 1752 defining a chamber 1754 extending between a first opening 1762 and a second opening 1764, and a diaphragm 1770 which closes or covers the first opening 1762 of the chamber 1754. The proximal end 1414 of the tube 1410 is connected to the body 1752 of the diaphragm pump assembly 1750 at the second opening 1764, such that the channel 1420 is in fluid communication with the chamber 1754. The body 1752 may further define one or more lugs 1768 configured to engage the flanges 1488 of the socket 1448 to couple the diaphragm pump assembly 1750 to the housing 1442.

In some embodiments, the body 1752 of the diaphragm pump assembly 1750 may include an inlet valve 1790 and outlet valve 1792, which may be configured in a similar manner to valves 1490 and 1492 as described in relation to tube unit 1401 and body 1452.

The diaphragm 1770 may be formed separately and held in place over the first opening 1762 of the chamber 1754 by a clamp 1772. For example, the clamp 1772 may comprise a threaded locking ring configured to threadedly engage the body 1752 thereby clamping a periphery of the diaphragm 1770 between the body 1752 and the clamp 1772, as shown in FIG. 17. In other embodiments, the diaphragm 1770 may be integrally formed with the body 1752, for example, using a composite moulding process.

The diaphragm 1770 comprises a resiliently deformable membrane which may be deformed by an actuator to change the volume of the chamber 1754 in fluid communication with the channel 1420 of the tube 1410. A central portion 1774 of the diaphragm 1770 may be removably coupled to the actuation rod 1446 of the driving mechanism 1444. The diaphragm 1770 includes a resiliently deformable portion 1776 surrounding the central portion 1774 allowing the central portion 1774 of the diaphragm to be moved back and forth relative to the body 1752 along an axis 1780 which is substantially normal (perpendicular) to a surface of the central portion 1774. For example, parallel to or in alignment with the axial motion of the actuation rod 1446 of the driving mechanism or linear motor 1444.

As the central portion 1774 of the diaphragm 1770 moves back and forth between a compressed position 1778*a* (shown in dashed lines) and a withdrawn position 1778*b* (shown in solid lines), the volume of the chamber 1754 is changed. Thus, the channel pressure in the tube 1410 can be adjusted and controlled by controlling the position of the actuation rod 1446 and central portion 1774 of the diaphragm 1770.

The diaphragm 1770 may be round or rotationally symmetric, but could define any suitable shape for a resiliently deformable membrane. The chamber 1754 is illustrated as a cylinder in FIG. 17, but may define any suitable shape for providing the desired range of channel pressure. In some embodiments, the chamber 1754 may be relatively short and taper towards the second end 1764 allowing for a relatively wide diaphragm 1770 and relatively narrow diameter of the second opening 1764, to allow a greater range of channel pressures for relatively little axial movement of the diaphragm.

In some embodiments, different tube units for different medical applications may be fitted with similar piston assemblies to allow each of the different tube units to be used with a common housing 1442 and motor 1444. In some embodiments, a plurality of tubes 1410 may be connected to a single piston assembly 1450 with the channel 1420 of each tube 1410 being in fluid communication with the cylinder 1454 of the piston assembly 1450.

Figure 15:
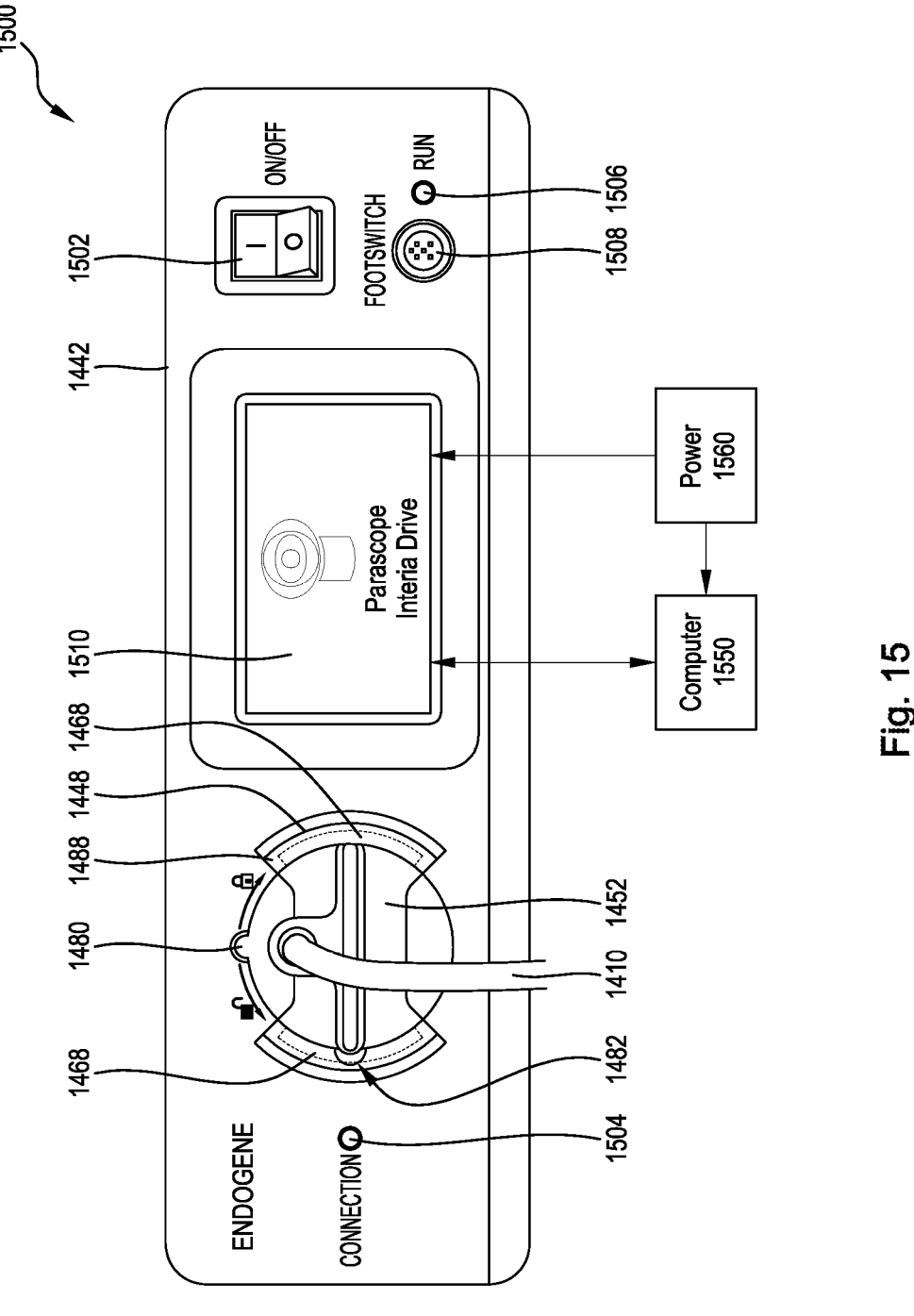
FIG. 15 shows a front panel of a drive console of the propulsion device of FIG. 14.

In some embodiments, the housing 1442 may comprise a drive console or drive unit 1500 as shown in FIG. 15. The drive console 1500 may comprise a power switch 1502 to control the supply of power to the drive console 1500 from a power source 1560.

The socket 1448 may comprise one or more circumferential flanges 1488 extending part way around a circumference of the socket and extending radially inward to retain the lugs 1468 of the body 1452 in the socket 1448. The lugs 1468 are shown in dashed lines in FIG. 15, projecting radially away from the body 1452 to be accommodated within or under the flanges 1488. The lugs 1468 also extend circumferentially around part of the body 1452.

Both the lugs 1468 and flanges 1488 are arranged such that there are gaps between the flanges 1488 to allow passage of the lugs 1468 and gaps between the lugs 1468 to allow passage of the flanges 1488 when coupling or decoupling the piston assembly 1450 to or from the socket 1448. To couple the piston assembly 1450 to the housing 1442, the body 1452 is inserted into the socket 1448 with the lugs 1468 aligned with the gaps between the flanges 1488, then the body 1452 is rotated to engage the lugs 1468 in a snug fit in a space defined between the flanges 1488 and a surface (not shown) of the housing 1442 that is opposed to and directly underlies the flanges 1488.

In some embodiments, the lugs 1468 and/or flanges 1488 may comprise a resilient click lock, clip or latch to secure the body 1452 against rotation in the connected alignment with the lugs 1468 engaged with the flanges 1488. The lugs 1468, and/or flanges 1488 may also comprise a stopper to restrict rotation of the piston assembly 1450 beyond the angle at which the lugs 1468 are fully engaged with the flanges 1488.

To decouple the piston assembly 1450 from the housing 1442, the body 1450 is rotated to disengage the lugs 1468 from the flanges 1488 with the lugs 1468 aligned with the gaps between the flanges 1488. Then the piston assembly 1450 can be removed from the socket 1448.

In some embodiments, the body 1450 may comprise an indicator tab 1480 to indicate the correct orientation when coupling the piston assembly 1450 to the socket 1448. The flanges 1488 may define a complimentary cut-out or recess 1482 configured to allow passage of the indicator tab 1480 when the piston assembly 1450 is correctly oriented for insertion into the socket 1448. Once inserted into the socket 1448, the body 1450 may be rotated, with the indicator tab passing under one or more of the flanges 1488, until the lugs 1468 are fully engaged with the flanges 1488. In some embodiments, the housing 1442 may comprise an indicia or marking to indicate the position of the indicator tab 1480 when the lugs 1468 are fully engaged with the flanges 1488.

The drive console 1500 may comprise a connection indicator light 1504 configured to light up when the piston assembly 1450 is connected to the drive console 1500. The drive console 1500 may comprise a sensor (not shown) to detect when the piston assembly 1450 is connected to the socket 1448 and/or when the lugs 1468 are fully engaged with the flanges 1488. When the sensor detects connection of the piston assembly 1450 to the drive console 1500, it may trigger a signal or complete an electrical circuit to turn on the connection indicator light 1504.

The drive console may comprise an operating indicator light or running indicator light 1506 configured to light up when the pressure actuator 1440 is in operation. The indicator light 1506 may be included in or linked to an electrical circuit controlling the supply of power to the motor 1444, such that the indicator light 1506 is turned on when the motor 1444 is in operation.

In some embodiments, the drive console 1500 may include a connection terminal 1508 configured to receive a connector of a signal cable from an external controller, such as a foot switch, for controlling operation of the pressure actuator 1440. In some embodiments, the drive console 1500 may include a display or user interface 1510 to provide information to a user regarding operations of the propulsion device 1400 and/or to allow the user to control operations of the propulsion device 1400. In some embodiments, the drive console 1500 may comprise a computer and/or controller 1550 configured to control operations of the propulsion device 1400.

The computer 1550 may be connected to the user interface 1510 to provide information about the operations of the propulsion device 1400 and, in some embodiments, may receive inputs from the user interface to select certain operating parameters. The user interface 1510 may comprise an intelligent display graphic user interface, and the computer 1550 may comprise a programmable microprocessor to control functions of the drive console 1500 and driving mechanism 1444. The power source 1560 may be connected to the drive console 1500 and computer 1550, and the computer 1550 may control the supply of power to various components of the drive console 1500.

Referring to FIG. 16, an endoscopic system 1600 is shown according to some embodiments. The endoscopic system 1600 comprises an endoscope 1601 having an insertion tube 1610 for insertion into a patient; an endoscope console 1620 for controlling operations of the endoscope; an endoscope handpiece 1630 for further and/or alternative control of operations of the endoscope 1601; a propulsion device 1400 for progressing the endoscope 1601 and insertion tube 1610 along a passage within a patient; and a power source (not shown) to supply power to the drive console 1500 and endoscope console 1620.

The propulsion device 1400 comprises a propulsion tube 1410 for insertion into the insertion tube 1610 as described above and a drive console 1500 to control operations of the propulsion device 1400.

The endoscopic system 1600 may further comprise a monitor 1640 configured to display images received from a camera of the endo scope via the endoscope console 1620.

The propulsion device 1400 may be operated to provide a propulsive force to the endoscope 1601 and insertion tube 1610 via momentum transfer in the propulsion tube 1410, as described above. The propulsive force may be used to progress the endoscope 1601, insertion tube 1610 and propulsion tube 1410 along a passage within a patient.

As the momentum is transferred to the propulsion tube 1410 along its length, there may be a reduced risk of the insertion tube 1610 getting stuck or reduced resistance as it navigates turns of the passage (e.g. turns of the gastrointestinal tract), as can often occur with conventional push-type endoscopes. This method of propulsion may also reduce friction at each turn as the endoscope progresses along the passage, as it provides an alternative to simply pushing the endoscope against each turn to further progress the endoscope, as is done with conventional push endoscopes.

In some embodiments, the propulsion device 1400 may be able to progress the endoscope 1601 along the passage at advancement speeds of about 1.5 cm/s, for example. Depending on various operational circumstances, conditions, and/or requirements, the advancement speed may be varied in the range of 0.1 cm/s to 2 cm/s, or 0.5 cm/s to 1 cm/s, for example. In some applications, the time-pressure profile may be reversed to move the tube 1410 backwards along the passage, for example, to assist in withdrawing the tube 1410 from the passage. The propulsion device 1400 may also allow for an improved completion rate for intestinal endoscopy, by allowing the endoscope 1601 to be progressed further or entirely along the length of the intestines to allow the full extent of the small intestine to be examined. The propulsion device 1400 may also allow access to the entire gastro-intestinal tract via endoscopy.

In various embodiments, the propulsion device 100, 1400, 1700 may be configured for progressing along a passage any one or more of: an instrument, probe, sensor, camera, monitoring device, tool, surgical tool, mining tool, drilling tool, endoscope, enteroscope, duodenoscope, borescope, robot tether, and industrial endoscope, for example. The propulsion device 100, 1400, 1700 may be configured to assist in progressing an instrument, sensor or tool along any one or more of: a passage, mine shaft, well bore, pipe, sewer, wall cavity, and passage in a patient, such as a lumen of a biological passage, artery or tract.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A propulsion device for progressing an instrument along a passage, the propulsion device comprising:
    an elongate tube comprising a first end and a second end opposite the first end, the tube defining a channel configured to accommodate a liquid, a first end of the channel being closed at or near the first end of the tube and a second end of the channel being defined by the second end of the tube; and
    a pressure actuator in communication with the second end of the channel and configured to selectively adjust a pressure of the liquid in the channel to alternatingly:
        reduce the pressure to induce cavitation and form gas bubbles in the liquid; and
        increase the pressure to collapse some or all of the gas bubbles back into the liquid, thereby accelerating at least part of the liquid towards the first end of the tube and transferring momentum to the tube to progress the tube along the passage.

2. The propulsion device of claim 1, further comprising one or more mechanisms configured to promote cavitation in one or more regions of the channel when the pressure is reduced, wherein the one or more regions extend along at least part of a length of the channel.

3. The propulsion device of claim 2, wherein the one or more mechanisms are configured to promote cavitation in a plurality of regions spaced along at least part of the length of the channel.

4. The propulsion device of claim 2, wherein the one or more mechanisms comprise a surface variation on an internal surface of the channel.

5. The propulsion device of claim 4, wherein the surface variation comprises a coating.

6. The propulsion device of claim 5, wherein the coating comprises a hydrophobic material.

7. The propulsion device of claim 4, wherein the surface variation comprises a topographical variation.

8. The propulsion device of claim 7, wherein the topographical variation comprises a scratched or pitted surface.

9. The propulsion device of claim 7, wherein the topographical variation defines a plurality of V-shaped channels.

10. The propulsion device of claim 7, wherein the topographical variation defines a porous surface.

11. The propulsion device of claim 2, wherein the one or more mechanisms comprise a variation in a thermal conductivity of a wall of the tube along the length of the channel.

12. The propulsion device of claim 2, wherein the one or more mechanisms comprise one or more acoustic transducers.

13. The propulsion device of claim 1, wherein the device is configured for progressing a medical instrument along a lumen within a patient.

14. The propulsion device of claim 1, wherein the tube is reinforced against expansion or contraction due to internal pressure changes.

15. The propulsion device of claim 1, further comprising a plurality of the tubes of claim 1 extending side by side.

16. The propulsion device of claim 1, wherein the pressure actuator comprises:
    a piston assembly including a moveable piston disposed within a bore of the piston assembly; and
    a driving mechanism configured to drive the piston of the piston assembly to selectively adjust the pressure of the liquid in the channel.

17. The propulsion device of claim 16, wherein the piston assembly is connected to the tube to form a sealed tube unit containing the liquid, and wherein the piston assembly is removably coupleable to the driving mechanism.

18. A propulsion tube unit comprising:

one or more of the tubes according to claim 1; and a piston assembly connected to the second end of the tube, the piston assembly comprising:

a body defining a bore in fluid communication with the channel of each of the one or more tubes; and a movable piston disposed within the bore and configured to seal against an internal surface of the bore.

19. The propulsion tube unit of claim 18, wherein the piston assembly and the one or more tubes cooperate to define a sealed vessel containing a selected mass of liquid and a selected mass of gas.

20. A method of progressing an instrument along a passage, the method comprising selectively adjusting a pressure of a liquid within a tube connected to the instrument to successively induce cavitation of gas bubbles in the liquid and subsequently collapse the gas bubbles back into the liquid to accelerate the liquid within the tube, transfer momentum from the liquid to the tube, and progress the tube along the passageway.

* * * * *